US006562575B1

(12) United States Patent
Dahl

(10) Patent No.: US 6,562,575 B1
(45) Date of Patent: May 13, 2003

(54) ANALYTE-SPECIFIC ASSAYS BASED ON FORMATION OF A REPLICASE SUBSTRATE

(75) Inventor: Gary A. Dahl, Madison, WI (US)

(73) Assignee: Epicentre Technologies Corporation, Madison, WI (US)

( * ) Notice: Subject to any disclaimer, the term of this patent is extended or adjusted under 35 U.S.C. 154(b) by 0 days.

(21) Appl. No.: 09/891,661

(22) Filed: Jun. 26, 2001

Related U.S. Application Data

(60) Provisional application No. 60/214,100, filed on Jun. 26, 2000.

(51) Int. Cl.⁷ ............................ C12Q 1/68; C12P 19/34
(52) U.S. Cl. ........................................ 435/6; 435/91.1
(58) Field of Search .................. 435/6, 91.2, 91.1, 435/91.21, 91.51, 91.52, 810

(56) References Cited

U.S. PATENT DOCUMENTS

| 4,786,600 A |   | 11/1988 | Kramer et al. |
| 4,957,858 A |   | 9/1990  | Chu et al. |
| 5,312,728 A |   | 5/1994  | Lizardi et al. |
| 5,364,760 A |   | 11/1994 | Chu et al. |
| 5,464,744 A |   | 11/1995 | Farrell et al. |
| 5,472,840 A | * | 12/1995 | Stefano ........................ 435/6 |
| 5,503,979 A |   | 4/1996  | Kramer et al. |
| 5,556,751 A |   | 9/1996  | Stefano |
| 5,556,769 A |   | 9/1996  | Wu et al. |
| RE35,443 E  |   | 2/1997  | DiFrancesco et al. |
| 5,620,870 A |   | 4/1997  | Kramer et al. |
| 5,631,129 A | * | 5/1997  | Chu et al. ..................... 6/22.1 |
| 5,652,107 A |   | 7/1997  | Lizardi et al. |
| 5,686,243 A |   | 11/1997 | Royer et al. |
| 5,750,338 A |   | 5/1998  | Collins et al. |
| 5,759,773 A | * | 6/1998  | Tyagi et al. .................... 435/6 |
| 5,763,171 A |   | 6/1998  | Stefano |
| 5,780,273 A |   | 7/1998  | Burg |
| 5,800,994 A |   | 9/1998  | Martinelli et al. |
| 5,807,674 A |   | 9/1998  | Tyagi |
| 5,959,095 A | * | 9/1999  | Martinelli et al. ....... 536/24.32 |
| 6,001,570 A |   | 12/1999 | Grossman |
| 6,090,589 A | * | 7/2000  | Dimond et al. ............ 435/91.1 |

FOREIGN PATENT DOCUMENTS

| EP | 0519053 B1  | * | 12/1991  | .................. 435/6 |
| EP | 0 519 053 B1 |   | 10/1997 | |

OTHER PUBLICATIONS

T. Blumenthal and G.G. Carmichael, "RNA Replication: Function and Structure of Q(beta)–Replicase," Ann. Rev. Biochem. 48:525–548, 1979.
P.M. Lizardi, et al., "Exponential Amplification of Recombinant–RNA Hybridization Probes," Bio/Technology 6:1197–1202, 1988.
S. Tyagi, et al., "Extremely Sensitive, Background–free Gene Detection Using Binary Probes and Q(beta) Replicase," Proc. Natl. Acad. Sci. USA 93:5395–5400, 1996.

* cited by examiner

Primary Examiner—Kenneth R. Horlick
(74) Attorney, Agent, or Firm—Quarles & Brady LLP

(57) ABSTRACT

Methods and compositions are provided for assaying for a target analyte in a sample by formation of a substrate for a replicase. The target analyte, if present in the sample, is first bound to a reporter probe. The reporter probe comprises a first portion and a second portion. The first portion comprises a polynucleotide that encodes at least part of a sequence for an RNA that is a substrate for replication. The second portion comprises a molecule that has affinity for an analyte. The reporter probe itself is not a substrate for a replicase. However, a replicase substrate is generated by treating reporter probe which is bound to analyte with a composition having nuclease activity in order to release the parts of the first portion, and then the released parts and one or more mononucleotides or oligonucleotides comprising missing parts of the substrate sequence are joined with a composition having ligase activity. Newly formed substrate is replicated with a replicase, and a signal is measured which indicates the presence and quantity of analyte in the sample. The invention also provides methods and compositions for simultaneously assaying for any of multiple analytes in a sample.

22 Claims, 6 Drawing Sheets

FROM FIG. 1A

Treat with a Nuclease to Release the Parts of the First Portion of the Reporter Probe & Then Ligate the Parts Substrate for Replication from First Portion Incubate with a Replicase for Replication of the Substrate Encoded by the First Portion of the Reporter Probe Detect Products Configuration
1  
2 FIG. 2B 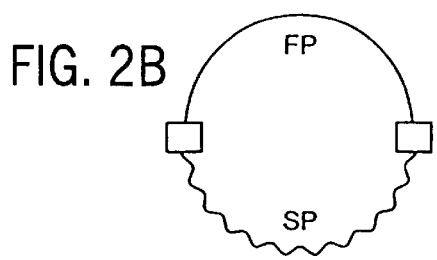
3  
4 FIG. 2D 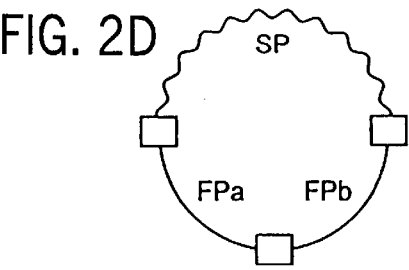 FIG. 2E 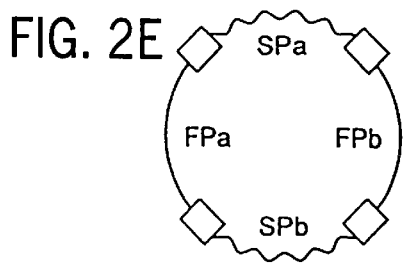
5 FIG. 2F 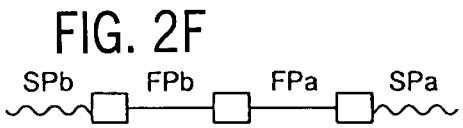 FIG. 2G 
6 FIG. 2H 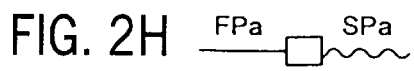 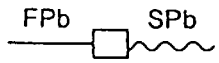

ANALYTE-SPECIFIC ASSAYS BASED ON FORMATION OF A REPLICASE SUBSTRATE

CROSS REFERENCE TO RELATED APPLICATIONS

This application claims priority to U.S. Provisional Application No. 60/214,100 filed Jun. 26, 2000, which is hereby incorporated by reference.

STATEMENT REGARDING FEDERALLY SPONSORED RESEARCH OR DEVELOPMENT

Not applicable.

BACKGROUND OF THE INVENTION

The present invention relates to assays for sensitive and specific detection of analytes in biological, environmental, pharmaceutical, or industrial samples. Such assays have broad applicability for detection of infectious agents, including bacteria, viruses, fungi, parasites, and other organisms, and for analyzing normal or aberrant genes or gene expression. These assays are useful in fields including human and veterinary medicine, water and environmental quality, food safety, identification of the source of nucleic acids found in forensic samples, as well as paternity testing, and for improvement of plant and animal agricultural products.

Throughout this application, various patents, published patent applications and other publications are referenced and citations provided for them. The disclosures of these publications in their entireties are hereby incorporated by reference into this application in order to more fully describe the state of the art to which this invention pertains.

A variety of methods are used in the art to detect and analyze analytes in biological samples. These methods include, among others, methods to identify and distinguish polynucleotide sequences, such as nucleic acid hybridization, methods to increase the quantity of polynucleotides, such as polymerase chain reaction or PCR (U.S. Pat. Nos. 4,683,195; 4,683,202; and 4,965,188), nucleic acid sequence based amplification or NASBA (U.S. Pat. Nos. 5,409,818; 5,130,238; and 5,554,517), transcription-mediated amplification or TMA (U.S. Pat. No. 5,437,990), self-sustained sequence replication or 3SR (Fahy, et al., PCR Methods & Appl. 1: 25–33, 1991), ligation chain reaction or LCR (e.g., U.S. Pat. Nos. 5,494,810 and 5,830,711), continuous amplification reaction or CAR (U.S. Pat. No. 6,027,897), linked linear amplification of nucleic acids or LLA (U.S. Pat. No. 6,027,923) and strand displacement amplification or SDA (U.S. Pat. Nos. 5,455,166; 5,712,124; 5,648,211; 5,631,147), and methods to increase a signal produced in the presence of a polynucleotide, such as rolling circle amplification or RCA (U.S. Pat. No. 5, 854, 033), cycling probe reaction or CPR (e.g., U.S. Pat. Nos. 4,876,187 and 5,011,769 and 5,660,988), branched chain amplification (e.g., U.S. Pat. Nos. 4,775,619 and 5,118,605 and 5,380,833 and 5,629,153). Many of these methods are discussed by Brow, et al. in U.S. Pat. No. 6,001,567, which is incorporated herein by reference.

Much work has also been done on using Q-beta (Q-beta) replicase, an RNA-dependent RNA polymerase for increasing the quantity of a polynucleotide or amplifying a signal produced in its presence (e.g., see U.S. Pat. Nos. 4,786,600; 4,957,858; 5,112,734; 5,118,801; 5,312,728; 5,356,774; 5,364,760; 5,472,840; 5,503,979; 5,556,751; 5,556,769; 5,602,001; 5,616,459; 5,620,851; 5,620,870; 5,629,156; 5,631,129; 5,652,107; 5,686,243; 5,750,338; 5,759,773; 5,763,171; 5,763,186; 5,780,273; 5,800,994; 5,807,674; 5,837,466; 5,871,976; 5,959,095; 6,001,570; European Patent Nos. 0266399; 0346594; 0386228; 0436644; 0473693). Some researchers believe it is the most sensitive system known.

Methods using Q-beta replicase have been proposed for detecting of a wide variety of analytes, including nucleic acids (DNAs and RNAs) and segments of nucleic acids; proteins, including glycoproteins and lipoproteins, enzymes, hormones, receptors, antigens, and antibodies; and polysaccharides. For example, Chu, et al. (U.S. Pat. Nos. 4,957,858 and 5,364,760) disclosed methods in which a substrate for Q-beta replicase was attached by various methods to an affinity molecule for an analyte. Following binding of the affinity molecule to the analyte and washing to remove unbound affinity molecules, the substrate was released from the affinity molecule by various method and was replicated by Q-beta replicase. Thus, replication of the substrate served as signaling system for the presence of the analyte. Most of the other work with Q-beta replicase has been limited to detecting nucleic acid analytes.

Q-beta replicase is remarkable because, from a small number of template strands, it can initiate in vitro synthesis of a large number of product strands (Haruna, I., and Spiegelman, S., Proc. Nat. Acad. Sci. USA, 54: 579–587, 1965; Science, 150: 884–886, 1965). A 100,000-fold increase in RNA can occur during a ten-minute reaction (Kramer, F. R., et al., J. Mol. Biol., 89: 719–736, 1974). This striking amplification is the consequence of an autocatalytic reaction mechanism. Single-stranded RNAs serve as templates for the synthesis of complementary single-stranded products. Both the product strand and the template strand are released from the replication complex and are free to serve as templates in subsequent rounds of synthesis. Consequently, the number of RNA strands increases exponentially as the reaction proceeds. The autocatalytic reaction proceeds at an exponential rate until the number of autocatalytically replicatable RNA molecules exceeds the number of active enzyme molecules in the reactions. After that point, the amount of autocatalytically replicatable RNA increases linearly with time. As a consequence, in reactions given a sufficient period of time to reach this linear phase (for example 15 minutes for 100 molecules), the amount of amplified product RNA will be directly related to the logarithm of the number of autocatalytically replicatable RNAs initially added (Lizardi, et al., Nature Biotechnology, 6: 1197–1202, 1988). Since the initial number of autocatalytically replicatable RNA probes is proportional to the amount of target, the amount of target present in the sample being examined may be quantified over a very wide range.

In vitro, Q-beta replicase can utilize a number of other RNA molecules besides the Q-beta genome as templates. One such template, termed midivariant RNA (MDV), discovered as a naturally occurring product in Q-beta replicase reactions, has been used for making amplifiable reporter probes for nucleic acid hybridization assays (e.g., U.S. Pat. No. 4,786,600). These reporter probes were made by inserting a target-specific probe sequence into an MDV molecule in a site such that it: 1) permits the MDV probe to specifically hybridize to its intended target nucleic acid, and 2) remains replicatable by Q-beta replicase in spite of the additional probe sequence. The MDV serves as an amplifiable detection ligand. One billion or more progeny molecules can be produced from a single starting template recombinant MDV molecule in approximately 30 minutes. Thus, a very large number of detection ligands (MDV RNA molecules) can be produced from very few hybridized reporter probes.

Theoretically, this permits the development of extremely sensitive nucleic acid hybridization assays; that is, assays which are capable of detecting the presence of very few target molecules (or organisms) in a test sample. However, assay sensitivity is a function not only of the amount of signal that can be generated for a given amount of target nucleic acid, but also of the amount of "background" signal that is generated even in the absence of target nucleic acid. The presence of background limits the sensitivity of assays at low target concentrations. Target induced signal must be significantly greater than background in order for assays to be considered reliable. Background has been a serious problem for assays using Q-beta replicase, in part because even a single replicatable RNA molecule will be replicated by the enzyme at an exponential rate.

For example, although Lizardi et al. (Nature Biotechnology, 6: 1197–1202, 1988) showed that MDV-1 RNA with a sequence for a protozoan parasite embedded within it was capable of exponential amplification by Q-beta replicase, they concluded that "practical assays employing recombinant RNAs did not exist yet" using this method because nonspecifically bound probes served as templates for amplification. According to the methods and format used, the recombinant RNA probes bound to the hybridization surface in sufficient quantities to be amplified by Q-beta replicase even in the absence of the protozoan target. They suggested that other methods were necessary for lowering the level of "background" signal due to nonspecifically bound recombinant RNA probes.

In addition to the problem of background due to nonspecific binding, researchers using heterologous sequences embedded within replicable Q-beta substrates like MDV also encountered another problem: the probe sequence is viewed as foreign by the enzyme and affects the ability of the RNA to be efficiently replicated, or is spontaneously deleted during replication. Deletion events affect the rate of replication and occur randomly with time. When deletion events occur, the level of the RNA products obtained in the linear phase of the amplification cannot be used to assess target level. Also, a further type of background, common with autocatalytically replicatable amplification systems, is "unprimed" activity of the enzyme itself (i.e., the enzyme makes new templates from mononucleotides de novo).

Q-beta replicase is composed of one phage-encoded subunit and three host-encoded subunits (Blumenthal, T. and Carmichael, G. G., Ann. Rev. Biochem., 48: 525–548, 1979). One source of background originates with the enzyme itself. For example, Q-beta replicase synthesizes new RNA species in the absence of extraneously added substrate (Biebricher, C. K., and Luce, R., Biochemistry, 32:4848–4854, 1993). No matter how poorly the new RNA replicates, once formed, it is amplified and optimized, although in an irreproducible manner. The products differ from experiment to experiment even when conditions are identical. This "evolution" of RNA molecules toward those which are more optimized for replication occurs by random addition of nucleotides to the ends of the new RNAs, by mutation, which can occur at an elevated rate, and by recombination of RNA molecules (Munishkin, A.V., et al., J. Mol. Biol., 221: 463–472, 1991; Biebricher, C. K., and Luce, R., EMBO Journal, 11: 5129–5135, 1992).

Another significant source of background signal in nucleic acid probe systems using Q-beta replicase has been the presence in some Q-beta replicase preparations of contaminating RNA termed "wild-type" or "endogenous" variant RNAs, which probably originated as just discussed, and which require use of special purification protocols to remove (e.g., see DiFrancesco, U.S. Pat. No. Re.35,443).

U.S. Pat. No. 5,750,338, attempted to reduce background due to nonspecific binding of the probe to solid supports using a method by which the target-probe complex was reversibly bound to the support ("reversible target capture"). After hybridization and immobilization, the complex is eluted from the support, which is then discarded with the nonspecifically bound probe. The target-probe is then recaptured on fresh support. This process may be repeated several times to produce a significant reduction in the amount of non-hybridized probe. The method is difficult and tedious, and usually did not reduce background sufficiently to achieve the sensitivity that is desired from such assays.

In U.S. Pat. Nos. 5,364,760 and 4,957,858, Chu et al. disclosed other methods to try to reduce background and develop sensitive analyte-specific assays using Q-beta replicase. For example, Chu et al. disclosed the use of "smart" probes. These probes were called "smart" because, ideally, the replicative RNA of a hybrid is replicated by the RNA-dependent RNA polymerase if and only if the affinity molecule portion hybridized to its analyte and the replicative RNA portion was released. That this was not completely successful is indicated by the inventors' statement that this occurs "but for unavoidable "non-specific binding" of affinity molecule or replicative RNA (via the RNA portion or first linking moiety portion thereof), which give rise to "background"." In addition, the synthesis of many of the probes that they used required several steps, increasing the cost and labor to produce them, and many contained disulfide linkages, which can be cleaved prematurely by reducing agents, such as glutathione, which occur naturally in biological samples, and which could lead to nonspecific signals.

In U.S. Pat. No. 5,763,171, Stefano discloses a method for detecting the presence of target nucleic acid in a sample using probes comprising a first section that is replicatable in the presence of an RNA-directed RNA polymerase, such as Q-beta replicase, and a second section that makes the first section incapable of replication. Ideally, the presence of a target sequence in a sample, in the presence of a release agent, results in target-specific release of the first section in a form that can be replicated by the RNA-directed RNA polymerase. Then, the released first section, which can be, for example MDV-1 RNA, is replicated under suitable reaction conditions and detected by some method known in the art. According to Stefano, the release method may take many forms, such as, by way of example, the enzyme RNase H or a ribozyme. Ideally, the first section of the probe is separated from or released from the second section only in the presence of the target sequence.

The state of the art at the time of filing of Stefano's "171" patent (see U.S. Pat. No. 5,763,171 and references therein), taught that linking a target-complementary sequence to either the 3'-end or the 5'-end of an autocatalytically replicatable RNA, such as MDV-1, via the phosphodiester linkage normally found in RNAs "has been reported to strongly inhibit replication" by an RNA-directed RNA polymerase like Q-beta replicase. Since then, additional work in the art has demonstrated that replicatable RNAs having a polynucleotide linked via a phosphodiester bond to its 5'-end can still be substrates for replication by Q-beta replicase. Also, although attaching a polynucleotide via a phosphodiester bond to the 3'-end of a replicatable RNA may inhibit replication, this inhibition is somehow quickly overcome. It is believed in the art that this occurs by replication of the first strand, and then either, subsequent occasional premature termination during replication of the second strand (i.e., the Q-beta replicase enzyme occasionally "falls off" of the template before synthesis of a complete RNA strand), or by occasional random breakage of template or product RNA. In either case, a substrate for replication is generated. Also, the rate of regeneration of replicatable RNA substrates may be increased by another characteristic of Q-beta replicase: if the normal end sequences of the substrate are not present, as might occur by premature termination or breakage of RNA, one enzymatic activity of Q-beta replicase is the random addition of nucleotides to the ends of the RNA. If any of these enzymatic activities results in even a single molecule of a "correct" or nearly correct (i.e., optimal) substrate, this substrate will be rapidly replicated and lead to a nonspecific signal.

It appears that Stefano also changed his ideas about the possibility of using a probe having a target-complementary sequence linked to either the 3'-end or the 5'-end of an autocatalytically replicatable RNA in the ways he envisioned in the "171" patent. In U.S. Pat. No. 5,556,751, which is a continuation-in-part of a patent filed later than the original patent application on which U.S. Pat. No. 5,763,171 is based, Stefano explicitly states that "if the probe sequence is appended to either end of the MDV sequence, then it is not replicated along with the MDV sequence." Thus, in U.S. Pat. No. 5,556,751, Stefano proposed assays in which a target-complementary probe sequence was appended to the 3'-terminus of a propidium iodide-resistant MDV sequence because he by then realized and disclosed that the target-complementary sequence on the 3'-terminus is lost when the MDV-probe sequence is replicated by Q-beta replicase, even without using any kind of release method. He further states in the "751" patent: "The advantage of designing the MDV probes in this fashion is that the probe sequence does not also need to be resistant to the inhibitory agent, since it is not replicated by Q-beta replicase." Thus, the increased specificity and reduced background were not obtained as intended by the invention disclosed in the "171" patent.

Some of the problems that result in background and low signal to noise ratios using RNA-directed RNA polymerases have been addressed by using split probes. For example, U.S. Pat. No. 5,631,129 uses Q-beta replicase to extend an RNA primer through a short target region of about 20–500 nucleotides. Two RNA primers are prepared. The first primer contains the first 157 nucleotides (at the 5'-end) of the minus-strand of Q-beta MDV-1 RNA followed by 10–50 nucleotides that are complementary to the target RNA over a region extending 5' from the 3' end of the site of the target sequence. The second primer contains the first 61 nucleotides (at the 5' end) of the plus-strand of Q-beta MDV-1 RNA followed by 10–50 nucleotides that are identical to the target RNA over a region extending 3' from the 5'-end of the target sequence. The two primers are hybridized to a target sequence, if present in a sample, and primer extension occurs in the presence of Q-beta replicase. Then, the second primer-extension product is released from the template by heating to 70° C. for 1 minute and quick-cooling on ice. Another aliquot of Q-beta replicase is added and amplification of the target RNA then proceeds autocatalytically by incubating at 37° C. for 20 min. The resulting mixture can then be assayed for the production of MDV-1 RNA that contains an insert that corresponds to the desired target sequence. Thus, the method uses portions of autocatalytically replicatable RNAs and results in the production of recombinant replicatable RNAs, permitting amplification of a target nucleic acid of interest.

Although the primer extension method of U.S. Pat. No. 5,631,129 should reduce background signal, the activity of Q-beta replicase in primer extension appears to be very low. Since double-stranded RNA is not a template for replication by Q-beta replicase, the 70° C. denaturation step may be required for replication. The method also appears to have some of the same disadvantages as PCR, which is influenced by many variables. For example, target DNA length and secondary structure, primer length, specificity and design, primer and dNTP concentrations, and buffer composition can all affect PCR and would be expected to influence primer extension prior to replication by Q-beta replicase.

In U.S. Pat. No. 5,759,773, Tyagi, et al. described still another approach. Tyagi et al. designed "binary probes" which consisted of two separate molecules, neither of which could be amplified by itself because neither contained all of the elements of sequence and structure that were required for replication by Q-beta replicase. Each probe contained half of an MDV substrate and part of a target-complementary sequence. The target-complementary sequences of the two probes were contiguous when hybridized to the target. Thus, ligation of the two binary probes when they were hybridized to the target resulted in a complete recombinant MDV that was capable of replication in the presence of Q-beta replicase. Since non-hybridized probes that were not aligned on a target had a very low probability of being ligated in solution, the background was reduced. The inventors also used other steps, such as cleavable capture probes to release hybrids from surfaces, to reduce background still further. Somewhat similarly, U.S. Pat. No. 5,959,095 utilized DNA binary MDV probes which contained contiguous target-complementary sequences, and one of which served to immobilize the target on the surface. The ligated recombinant MDV DNA was transcribed into RNA, using a phage promoter sequence on one of the binary MDV probes before replication with replicase.

The binary probe method of Tyagi et al. (U.S. Pat. No. 5,759,773) appears to have promise. The only apparent problems are the amount of labor involved to perform the number of steps involved and the potential for background due to nonspecific ligation; since the thermostable ligases which are currently used for LCR are not active on RNA, additional work is required before assays with RNA probes can be carried out at higher temperatures and higher stringency. The lability of RNA at elevated temperature increases the difficulty of developing such assays, and argues in favor of binary DNA probes, as described in U.S. Pat. No. 5,959,095. However, based on past experience, it is likely that the methods of Tyagi et al. will have lower backgrounds than methods involving ligation of probes hybridized to a surface.

In European Patent No. EP 051 9053B1, Dimond et al. also disclosed some methods using split or binary probes which are similar to those described in U.S. Pat. Nos. 5,631,129 and 5,759,773 discussed above, except that Dimond et al. used "complex templates" which comprise at least one 2'-deoxyribonucleotide instead of RNA templates. Their disclosures were based on the fact that Q-beta replicase also has DNA-dependent RNA polymerase activity in the presence of greater than 0.5 mM concentration of manganese, cobalt or zinc divalent cations. In addition to disadvantages of the methods of U.S. Pat. Nos. 5,631,129 and 5,759,773, the assays of Dimond et al. are likely to also suffer from decreased reaction rates and lower specificity and accuracy compared to assays using Q-beta replicase in the presence of magnesium divalent cations. For example, as reviewed by Blumenthal and Carmichael (Ann. Rev. Biochem., 48: 525–548, 1979), adding manganese to the reaction mixture is one of the ways to overcome the template specificity of Q-beta replicase.

The above background, including references cited herein, summarize the state of the art pertaining to the use of RNA-directed RNA polymerases such as Q-beta replicase as of the date of the present invention. This summary shows that RNA-directed RNA polymerases such as Q-beta replicase are remarkable in being able to exponentially amplify even a single molecule by a billion-fold or more in about 30 minutes. In the absence of nonspecific background signals, these assays would permit quantification of target polynucleotide sequences over a broad concentration range of target in a sample. However, the art also shows that the properties of RNA-directed RNA polymerases result in special problems that still must be dealt with and overcome in order to develop sensitive, but specific and meaningful assays to detect target nucleic acid sequences in a sample. Among the properties causing special difficulties are the following: (1) since even a single substrate molecule is amplified, steps must be designed to eliminate background due to nonspecific binding of substrate molecules to solid surfaces or other molecules in the assay reaction mixture and prevent carry-over contamination to subsequent assays; and (2) since target-complementary polynucleotide sequences or other eheterologous polynucleotide sequences that are inserted within a substrate for Q-beta replicase can be deleted during the replication reaction, and the amplification signal obtained need not be specific for the target, strategies must be implemented to ensure that the assay results are target-specific. In brief, the only assay methods which appear to have been successful using Q-beta replicase are those which use some form of a binary probe, such that different parts of a polynucleotide that are required for replication are joined together only in the presence of a target. Such assays include, for example, those disclosed in U.S. Pat. No. 5,631,129, U.S. Pat. No. 5,759,773 and No. 5,959,095, and some of the embodiments in European Patent No. EP0519053B1. However, as discussed above, even these latter assays require additional work to be accepted for routine use by those who work in the various fields of use of the present invention.

What is needed in the art are assays with the sensitivity of exponential amplification obtained with RNA-dependent RNA polymerases like Q-beta replicase, yet which are easier to control and design, and which yield lower backgrounds than assays which amplify both target and replicase substrate sequences.

What is needed in the art is a method that uses a replicase to generate a signal in a target-specific manner, but which does not amplify the target.

What is needed is a method for using a replicase which permits accurate quantification of the amount of an analyte in a sample.

What is needed is a method for using a replicase that permits multiplex assays for multiple analytes in a sample, including multiplex assays for accurate quantification of different analytes.

What is needed is a method for using a replicase that permits assays for a broad variety of analytes.

What is needed is a method that can be used in homogeneous assays for an analyte in a sample.

The above background, including references cited herein, being a general description of the state of the art pertaining to the present invention, we now summarize the invention below.

SUMMARY OF THE INVENTION

In this description and in the appended claims, I sometimes refer to a molecule in the singular (e.g., "a reporter probe"). The same applies to a complex (e.g., "a reporter probe-target hybrid"). It will be understood that many copies are in fact used or made. I sometimes utilize the plural rather than stating "copies of," which is cumbersome. Persons skilled in the art will understand the meaning from the context.

The assays of the present invention are signal amplification assays for detecting the presence of at least one analyte or, preferably, multiple analytes in a sample. The assays of the invention are also for quantifying analyte molecules in a sample, or for identifying analytes in a sample. These assays include at least one improvement, but preferably, a combination of improvements, to reduce background and improve sensitivity and specificity.

The present invention comprises compositions and methods for assaying for an analyte in a sample, said methods comprising the steps of:

(a) incubating a sample with a reporter probe under conditions and for a time so as to permit binding of said reporter probe with analyte, if present in sample, said reporter probe comprising a first portion, wherein said first portion is a polynucleotide that encodes at least part of a sequence for a replicase substrate, and a second portion, wherein said second portion has affinity for the analyte under binding conditions, and wherein said reporter probe is not a substrate for replication by said replicase; and (b) incubating said reporter probe which binds to analyte with a composition having nuclease activity, wherein said composition releases all parts of said first portion of said reporter probe from said second portion of said reporter probe; and (c) incubating said released parts of said first portion of said reporter probe with a composition having ligase activity so as to form a polynucleotide which encodes a complete substrate for replication by a replicase, and providing conditions so as to generate said substrate; and (d) incubating said substrate with a replicase under replication conditions; and (e) detecting the products of said replication.

Preferred embodiments of the invention use a reporter probe comprising monoribonucleosides.

Embodiments of assays which use a reporter probe having a first portion comprising monodeoxyribonucleosides additionally comprise an in vitro transcription step in order to generate an RNA substrate for replication by a replicase.

Preferred embodiments of the invention are homogenous assays. In other preferred embodiments, unbound reporter probe molecules are separated from reporter probe molecules bound to analyte, if analyte is present in the sample, prior to contacting reporter probe molecules which are bound to analyte with a nuclease. Preferably, the separation is accomplished using at least one capture probe which binds to analyte and which can be immobilized on a surface.

The invention is not limited by the nuclease used to release the parts of the first portion of the reporter probe from the second portion of the reporter probe. Preferred embodiments use ribonuclease H (RNase H) or a 5' nuclease as the composition having nuclease activity, but other compositions can also be used.

The invention also includes assays for quantification of analytes, including, but not limited to, nucleic acid or polynucleotide analytes, over a broad concentration range of the analyte in a sample.

The invention further includes assays for simultaneous detection of the presence of any of multiple different target polynucleotide sequences in a sample.

The inventor believes, that in addition to solving the types of problems encountered using Q-beta replicase, the present invention also provides at least one advantage, and often multiple advantages, over other analyte-specific assays of the prior art. Among the advantages of the present invention for assays for nucleic acid analytes are the following:

1. The methods of the present invention do not involve nucleic acid synthesis using the target nucleic acid as a template. For methods involving DNA-dependent and/or RNA-dependent polymerization of a target sequence (e.g., PCR, NASBA, TMA, 3SR), the priming efficiency, priming specificity, target length, and processivity of polymerization can differ for different templates based on sequence and structure. Therefore, the primers and assay conditions must be carefully optimized for each target, and even so, the results vary for each template. These variables cause special difficulties in trying to quantify nucleic acid targets, especially for multiplex assays for multiple targets. Even for other assays using replicatable recombinant RNA probes in which different target-complementary sequences are inserted in a Q-beta replicase substrate like MDV-1 RNA, the replication efficiency of each probe usually differs, leading to differences in quantitative results.

Further, unless special methods and sample handling procedures are implemented in the user's laboratory, assays that comprise synthesizing a target nucleic acid sequence can result in spread of the amplified product to negative samples, which is referred to in the art as "carryover contamination." For example, it is well known that carryover contamination can be a serious problem for diagnostic laboratories that perform PCR assays routinely, and a variety of compositions and methods are available to try to avoid problems of PCR carryover contamination.

In contrast, the methods of the present invention are based on the well-understood principles of hybridization of complementary sequences and nuclease digestion using enzymes, such as ribonuclease H, which do not produce significantly different results for different target sequences. Since the RNA substrate encoded by the first portion of the reporter probe can be identical whatever target-complementary sequence is used in the second portion, quantification of different analytes is directly comparable.

Also, since the target nucleic acid is not synthesized in assays of the present invention and, in fact, the target-complementary sequence of the second portion is destroyed by nuclease digestion in most embodiments of the invention, there is no chance for carryover contamination of amplified target nucleic acid to other samples.

2. The assays of the present invention do not require thermocycling like assays such as PCR and LCR. The need for a thermocycler increases expense and availability of assays and limits the number of assays that can be performed to the capacity of the thermocycler.

In addition, thermocycling introduces numerous variables into the assays, which can have dramatic effects on specificity and sensitivity of assays. For example, each brand of thermocycler, and sometimes even each individual machine, can have different ramp times (i.e., different rates of change of temperature) and differences in temperature in different parts of the heating block, which can also change over time. Different thermostable enzymes, and even different preparations of the same enzyme, can have different activities and different half lives at any given temperature, and can be affected differently (e.g., inactivated by different amounts) by the temperature cycling. A relatively small difference in the relative enzyme activity or in the rate of enzyme inactivation during one cycle results in a large difference in amplification yield after multiple cycles. For example, in a PCR reaction with 30 amplification cycles and a 10% difference in yield per cycle, the difference in final yield would be more than 20-fold after 30 cycles. Depending on the amount of analyte in the sample and the sensitivity of the detection method used, this could be the difference between a positive assay and a false negative.

In contrast, the methods of the present invention do not use thermocycling. Since a thermocycler isn't needed, assays of the present invention are less expensive, and the number of assays that can be performed is not limited by availability or capacity of the thermocycler.

Also, most embodiments of the present invention do not use steps in which an enzyme component is exposed to an elevated temperature, minimizing the chance for enzyme inactivation or variability of assay results. All enzymatic steps of the present invention can be performed under isothermal conditions. In some embodiments, the assays can even be designed to be performed under "ambient" conditions (i.e., in the field). In those embodiments in which a higher temperature is used for certain steps in order to achieve a higher stringency, the steps are still carried out under isothermal conditions, so consistent results are obtained, and sample-to-sample quantification comparisons can be made.

3. The assays of the present invention produce low background signals and result in exponential amplification. The cycling probe reaction (CPR) generates a signal by ribonuclease H cleavage of each probe that hybridizes to the nucleic acid analyte, if analyte is present in the sample. Once a probe is cleaved, the resulting fragments are too short to remain hybridized to the analyte, permitting another probe to anneal and be cleaved, thereby increasing the signal. The maximum signal obtain is only about 1000-fold to 10,000-fold over background. The CAR assay, which relies on transcription, also does not result in signal amplification as high as can be obtained by PCR or NASBA.

In contrast, embodiments of the assays of the present invention use an exponential replication mechanism, resulting in highly sensitive assays because of production of large amounts of amplified RNA and a low background signals in the absence of a specific target analyte.

4. The assays of the present invention can be designed to detect analytes that are not nucleic acids. Most of the other assays discussed above use one or more steps that limits their ability to be used to detect analytes other than nucleic acids. The two exceptions are Q-beta replicase assays (U.S. Pat. Nos. 4,957,858 and 5,364,760) and some embodiments of Rolling Circle Amplification (U.S. Pat. No. 5,854,033).

In contrast to other assays, the present invention discloses how proven methods for making and using nucleic acids as analyte-binding substances can be used in assays to detect non-nucleic acid analytes. Thus, reporter probes and methods used for embodiments of the present invention for nucleic acid analytes can also be used to make sensitive and specific assays for other analytes of almost any composition. Also, the invention is not limited to reporter probes comprising nucleic acids for detection of non-nucleic acid analytes. By using a linking oligonucleotide to join the analyte-binding substance of the second portion of the reporter probe to the signal-producing substrate encoded by the first portion, a variety of non-nucleic acid analyte-binding substances can be used to make sensitive and specific assays for a variety of analytes.

It is an object of this invention to provide sensitive and specific assays for a variety of analytes.

It is a further object of the invention to provide assays that permit detection of any of multiple different analytes in the same sample.

It is a further object of the invention to provide assays that permit quantification of analytes over a broad range of analyte concentrations.

It is a further object of the invention to provide homogenous assays.

It is a further object to provide compositions and kits for performing the methods of the invention.

DETAILED DESCRIPTION OF THE INVENTION

Definitions

Figure 1A:
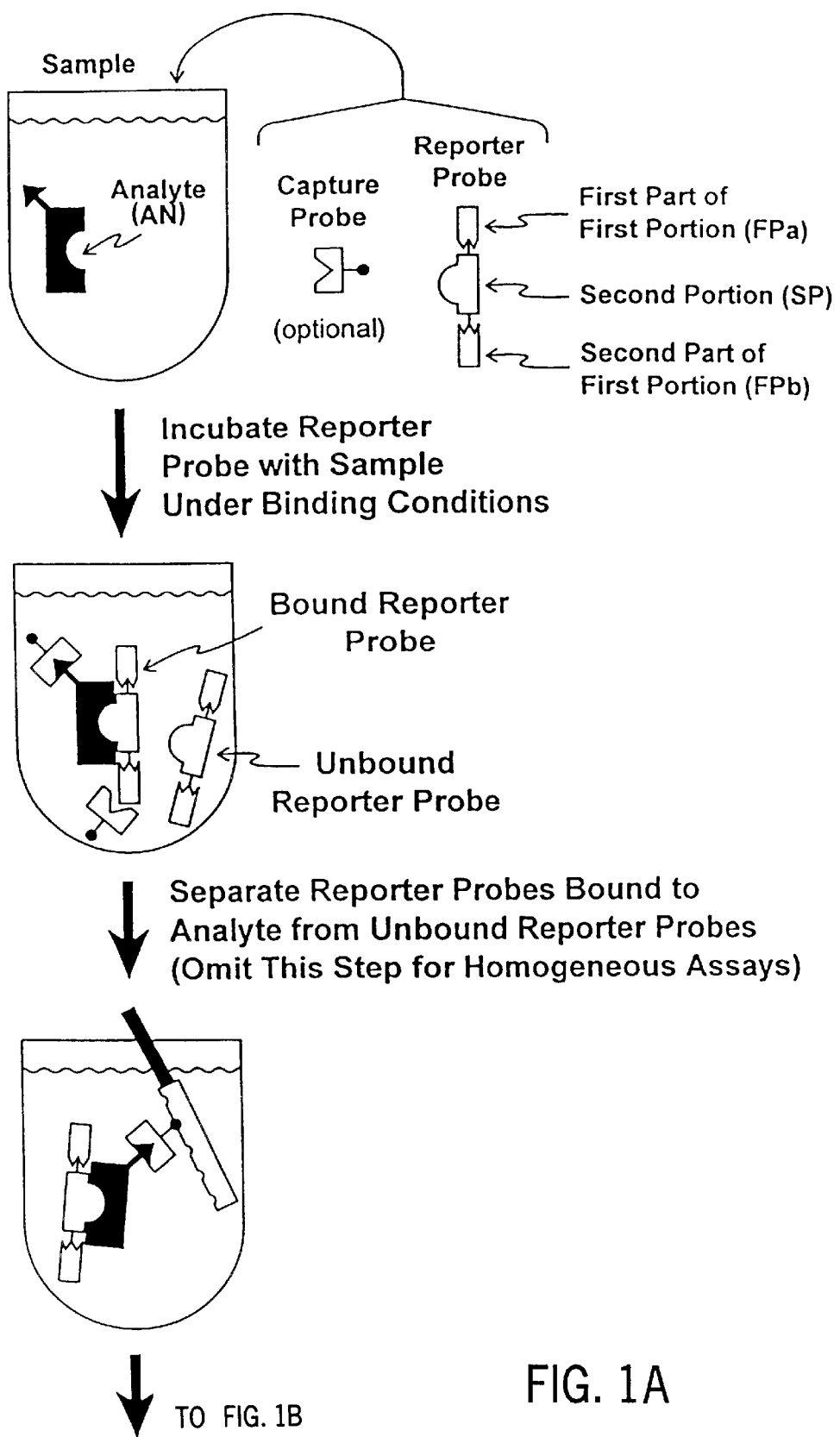
FIG. 1 is a schematic of a basic embodiment of the invention using a reporter probe comprising monoribonucleotides.
Figure 1B:
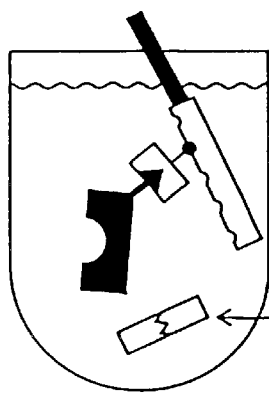
Figure 1B:
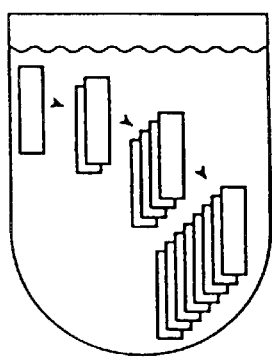
Figure 1B:
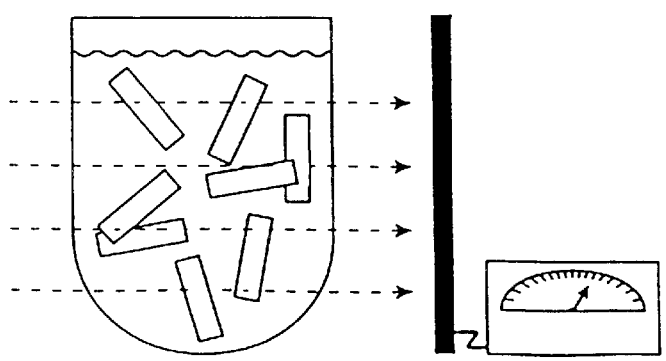

A variety of terms are used in describing the present invention. In most cases, only terms which are broad and apply to many aspects of the invention are presented in the "Definitions" section. Other terms are defined as presented in describing the specifications and claims in other sections, including, but not limited to, sections entitled "Detailed Description of the Invention," "Figures," and "Examples." If the same terms or similar terms have been used with different meaning by others, including those presented in the section entitled "Background to the Invention" herein above, the terms when used to describe the present invention, shall nevertheless be interpreted to have the meanings presented below and in the sections related to the specification and claims.

Samples and Analytes of the Invention

A "sample" according to the present invention is used in its broadest sense. A sample is any specimen that is collected from or is associated with a biological or environmental source, or which comprises or contains biological material, whether in whole or in part, and whether living or dead. Biological samples may be plant or animal, including human, fluid (e.g., blood or blood fractions, urine, saliva, sputum, cerebral spinal fluid, pleural fluid, milk, lymph, or semen), swabs (e.g., buccal or cervical swabs), solid (e.g., stool), microbial cultures (e.g., plate or liquid cultures of bacteria, fungi, parasites, protozoans, or viruses), or cells or tissue (e.g., fresh or paraffin-embedded tissue sections, hair follicles, mouse tail snips, leaves, or parts of human, animal, plant, microbial, viral, or other cells, tissues, organs or whole organisms, including subcellular fractions or cell extracts), as well as liquid and solid food and feed products and ingredients such as dairy items, vegetables, meat and meat by-products, and waste. Biological samples may be obtained from all of the various families of domestic plants or animals, as well as wild animals or plants.

Environmental samples include environmental material such as surface matter, soil, water, air, or industrial samples, as well as samples obtained from food and dairy processing instruments, apparatus, equipment, utensils, disposable and non-disposable items. These examples are not to be construed as limiting the sample types applicable to the present invention.

In short, a sample comprises a specimen from any source that contains or may contain a target analyte.

A sample on which the assay method of the invention is carried out can be a raw specimen of biological material, such as serum or other body fluid, tissue culture medium or food material. More typically, the method is carried out on a sample which is a processed specimen, derived from a raw specimen by various treatments to remove materials that would interfere with detection of analyte, such as by causing non-specific binding of affinity molecules. Methods of processing raw samples to obtain a sample more suitable for the assay methods of the invention are well known in the art.

An "analyte" means a substance whose presence, concentration or amount in a sample is being determined in an assay. An analyte is sometimes referred to as a "target substance" or a "target molecule" or a "target analyte" of an assay. An analyte may also be referred to more specifically. For an analyte that is a nucleic acid, for example, the analyte may be referred to as a "target nucleic acid" or a "target polynucleotide" or a "target sequence" or a "target oligonucleotide," depending on the particular case. With assays according to the present invention, the analyte is usually a biopolymer or a segment of a biopolymer, but it is not intended that the invention be limited to any specific analyte. Analytes include, for example, proteins, including glycoproteins and lipoproteins, enzymes, hormones, receptors, antigens and antibodies; nucleic acids (DNAs and RNAs); segments of nucleic acids; biochemical molecules; and polysaccharides.

With assays of the present invention, an analyte is often associated with a biological entity that is present in a sample if and only if the analyte is present. Such biological entities include viroids (analyte is, e.g., a nucleic acid or a segment thereof); viruses (analyte is, e.g., a viral coat protein, viral genome, or segment of viral genome, or antibody against the virus); other microorganisms (analyte is, e.g., a segment of the genome or the RNA of the microorganism, a toxin produced by the microorganism, or an heterologous protein made by the microorganism if it is genetically engineered; abnormal cells, such as cancer cells (analyte is, e.g., a cell surface antigen of the abnormal cell or an oncogene); or an abnormal gene (analyte is, e.g., a gene segment which includes the altered bases which render the gene abnormal, a messenger RNA segment which includes altered bases as a result of having been transcribed from the abnormal gene, or an abnormal protein product expressed from the abnormal gene). An analyte may also be a particular protein, such as, for example, a hormone, whose presence or concentration in serum or other body fluid is to be ascertained in an assay. In the case of immunoassays that entail the use of two antibodies, analyte may be antigen bound to first antibody (in the case of a sandwich assay) or first antibody bound to antigen (in the case of an immunosorbent assay). Many other types of analyte will be apparent to those skilled in the art.

From the description of analyte, it is apparent that the present invention has widespread applicability, including in applications in which immunoassays or nucleic acid probe hybridization assays are employed. Thus, among other applications, the invention is useful in diagnosing diseases in plants and animals, including humans; and in testing products, such as food, blood, and tissue cultures, for contaminants.

A "target" of the present invention is a biological organism or material that is the reason or basis for which a diagnostic assay is performed. By way of example, but not of limitation, an assay of the present invention may be performed to detect a target that is a virus which is indicative of a present disease or a risk of future disease (e.g., HIV which is believed to result in AIDS), or a target that is a gene which is indicative of antibiotic resistance (e.g., an antibiotic resistance gene in an infectious pathogenic bacterium), or a target that is a gene which, if absent, may be indicative of disease (e.g., a deletion in an essential gene). In developing assays according to the present invention, it is important to identify target analytes that yield assay results that are sufficiently specific, accurate, and sensitive to be meaningful related to the presence or condition of the target. A target analyte that is a "target polynucleotide" or a "target nucleic acid" of the present invention comprises at least one nucleic acid molecule or portion of at least one nucleic acid molecule, whether said molecule or molecules is or are DNA, RNA, or both DNA and RNA, and wherein each said molecule has, at least in part, a defined nucleotide sequence. The target polynucleotide contains a sequence that has at least partial complementarity with at least a portion of a reporter probe, and it may also have at least partial complementarity with other molecules used in an assay, such as, but not limited to, capture probes or to an invader oligonucleotide. The target polynucleotide may be single- or double-stranded. A target polynucleotide of the present invention may be of any length, except that it must comprise a polynucleotide sequence of sufficient sequence specificity and length so as to remain hybridized to a target-complementary sequence of a reporter probe under assay hybridization conditions wherein sequences that are not target polynucleotides are not hybridized. A target polynucleotide having sufficient sequence specificity and length for an assay of the present invention may be identified, using methods known to those skilled in the art, by comparison and analysis of nucleic acid sequences known for a target and for other sequences which may be present in the sample. For example, sequences for nucleic acids of many viruses, bacteria, humans (e.g., for genes and messenger RNA), and many other biological organisms can be searched using public or private databases, and sequence comparisons, folded structures, and hybridization melting temperatures (i.e., $T_m$'s) may be obtained using computer software known to those knowledgeable in the art.

The terms "source of target nucleic acid" or "source of target polynucleotide" refers to any sample that contains nucleic acids (RNA or DNA).

Thus, a method of the present invention can be carried out on nucleic acid from a variety of soureces, including nucleic acids purified using various "spin" columns, cationic membranes and filters, or salt precipitation techniques, for which a wide variety of products are commercially available (e.g., MASTERPURE DNA & RNA Purification Kits from Epicentre Technologies, Madison, Wis., USA). Methods of the present invention can also be carried out on nucleic acids isolated from viroids, viruses or cells of a specimen and deposited onto solid supports as described by Gillespie and Spiegelman (J. Mol. Biol. 12: 829–842, 1965), including solid supports on dipsticks and the inside walls of microtiter plate wells. The method can also be carried out with nucleic acid isolated from specimens and deposited on solid support by "dot" blotting (Kafatos, et al., Nucl. Acids Res., 7: 1541–1552, 1979); White, and Bancroft, J. Biol. Chem., 257: 8569–8572, 1982); Southern blotting (Southern, E., J. Mol. Biol., 98: 503–517, 1975); "northern" blotting (Thomas, Proc. Natl. Acad. Sci. USA, 77: 5201–5205, 1980); and electroblotting (Stellwag, and Dahlberg, Nucl. Acids Res., 8: 299–317, 1980). The method can also be carried out for nucleic acids spotted on membranes, on slides, or on chips as arrays or microarrays. Nucleic acid of specimens can also be assayed by the method of the present invention applied to water phase hybridization (Britten, and Kohne, Science, 161: 527–540, 1968) and water/organic interphase hybridizations (Kohne, et al., Biochemistry, 16: 5329–5341, 1977). Water/organic interphase hybridizations have the advantage of proceeding with very rapid kinetics but are not suitable when an organic phase-soluble linking moiety, such as biotin, is joined to the nucleic acid affinity molecule.

The assay methods of the present invention can also be carried out on nucleic acids obtained as products of another amplification reaction, such as, but not limited to, a nucleic acid obtained using PCR, NASBA, TMA, 3SR, LCR, CAR, LLA, SDA, RCA, or Invader. RTM. assays (e.g., U.S. Pat. No. 6,001,567). There are various reasons for using a nucleic acid that is a product of another assay as a target nucleic acid for an assay of the present invention, such as, but not limited to, for obtaining more sensitive detection of targets, greater specificity, or to decrease the time required to obtain an assay result.

The assay methods of the invention can also be carried out on proteins or polysaccharides isolated from specimens and deposited onto solid supports by dot-blotting, by "Western" blotting, or by adsorption onto walls of microtiter plate wells or solid support materials on dipsticks, on membranes, on slides, or on chips as arrays or microarrays.

Still further, the methods of the invention are applicable to detecting cellular proteins or polysaccharides on the surfaces of whole cells from a specimen or proteins or polysaccharides from microorganisms immobilized on a solid support, such as replica-plated bacteria or yeast.

Nucleic Acids and Polynucleotides of the Invention

A "nucleic acid" or "polynucleotide" of the invention is a polymer molecule comprising a series of "mononucleosides," also referred to as "nucleosides," in which the 3'-position of the pentose sugar of one nucleoside is linked by an intemucleoside linkage, such as, but not limited to, a phosphodiester bond, to the 5'-position of the pentose sugar of the next nucleoside. A nucleoside linked to a phosphate group is referred to as a "nucleotide." The nucleotide that is linked to the 5'-position of the next nucleotide in the series is referred to as "5' of," or "upstream of," or the "5' nucleotide" and the nucleotide that is linked to the 3'-position of said 5' or upstream nucleotide is referred to as "3' of," or "downstream of," or the "3' nucleotide." The pentose sugar of the nucleic acid can be ribose, in which case, the nucleic acid or polynucleotide is referred to as "RNA," or it can be 2'-deoxyribose, in which case, the nucleic acid or polynucleotide is referred to as "DNA." Alternatively, especially if the nucleic acid is synthesized chemically, the nucleic acid can be composed of both DNA and RNA mononucleotides. In both RNA and DNA, each pentose sugar is covalently linked to one of four common "nucleic acid bases" (each also referred to as a "base"). Three of the predominant naturally-occurring bases that are linked to the sugars (adenine, cytidine and guanine) are common for both DNA and RNA, while one base is different; DNA has the additional base thymine, while RNA has the additional base uridine. Those in the art commonly think of a small polynucleotide as an "oligonucleotide." The term "oligonucleotide" as used herein is defined as a molecule comprised of two or more deoxyribonucleotides or ribonucleotides, preferably about 10 to 30 nucleotides, but there is no defined limit to the length of an oligonucleotide. The exact size will depend on many factors, which in turn depends on the ultimate function or use of the oligonucleotide.

Also, for a variety of reasons, a nucleic acid or polynucleotide of the invention may comprise one or more modified nucleic acid bases, sugar moieties, or internucleoside linkages. By way of example, some reasons for using nucleic acids or polynucleotides that contain modified bases, sugar moieties, or internucleoside linkages include, but are not limited to: (1) modification of the $T_m$; (2) changing the susceptibility of the polynucleotide to one or more nucleases; (3) providing a moiety for attachment of a label; (4) providing a label or a quencher for a label; or (5) providing a moiety, such as biotin, for attaching to another molecule which is in solution or bound to a surface.

In order to accomplish these or other goals, the invention does not limit the composition of the nucleic acids or polynucleotides comprising reporter probes, capture probes, oligonucleotides, or other nucleic acids used or detected in the assays of invention, so long as each said nucleic acid functions for its intended use. By way of example, but not of limitation, the nucleic acid bases in the mononucleotides may comprise guanine, adenine, uracil, thymine, or cytidine, or alternatively, one or more of the nucleic acid bases may comprise xanthine, allyamino-uracil, hypoxanthine, 2-aminoadenine, 6-methyl and other alkyl adenines, 2-propyl and other alkyl adenines, 5-halouracil, 5-halo cytosine, 5-propynyl uracil, 5-propynyl cytosine, 7-deazaadenine, 7-deazaguanine, 7-deaza-7-methyl-adenine, 7-deaza-7-methyl-guanine, 7-deaza-7-propynyl-adenine, 7-deaza-7-propynyl-guanine and other 7-deaza-7-alkyl or 7-aryl purines, N2-alkyl-guanine, N2-alkyl-2-amino-adenine, purine 6-aza uracil, 6-aza cytosine and 6-aza thymine, 5-uracil (pseudo uracil), 4-thiouracil, 8-halo adenine, 8-amino-adenine, 8-thiol adenine, 8-thiolalkyl adenines, 8-hydroxyl adenine and other 8 substituted adenines and 8-halo guanines, 8-amino-guanine, 8-thiol guanine, 8-thiolalkyl guanines, 8-hydroxyl guanine and other 8 substituted guanines, other aza and deaza uracils, other aza and deaza thymidines, other aza and deaza cytosine, aza and deaza adenines, aza and deaza guanines or 5-trifluoromethyl uracil and 5-trifluorocytosine. Still further, they may comprise a nucleic acid base that is derivatized with a biotin moiety, a digoxigenin moiety, a fluorescent or chemiluminescent moiety, a quenching moiety or some other moiety. The invention is not limited to the nucleic acid bases listed; this list is given to show the broad range of bases which may be used for a particular purpose in an assay.

When a molecule comprising both a nucleic acid and a peptide nucleic acid (PNA) is used in the invention, modified bases can be used in one or both parts. For example, binding affinity can be increased by the use of certain modified bases in both the nucleotide subunits that make up the 2'-deoxyoligonucleotides of the invention and in the peptide nucleic acid subunits. Such modified bases may include 5-propynylpyrimidines, 6-azapyrimidines, and N-2, N-6 and O-6 substituted purines including 2-aminopropyladenine. Other modified pyrimidine and purine base are also expected to increase the binding affinity of macromolecules to a complementary strand of nucleic acid.

With respect to nucleic acids or polynucleotides of the invention, one or more of the sugar moieties can comprise ribose or 2'-deoxyribose, or alternatively, one or more of the sugar moieties can be some other sugar moiety, such as, but not limited to, 2'-fluoro-2'-deoxyribose or 2'-O-methyl-ribose, which provide resistance to some nucleases.

The internucleoside linkages of nucleic acids or polynucleotides of the invention can be phosphodiester linkages, or alternatively, one or more of the internucleoside linkages can comprise modified linkages, such as, but not limited to, phosphorothioate, phosphorodithioate, phosphoroselenate, or phosphorodiselenate linkages, which are resistant to some nucleases.

When two different, non-overlapping polynucleotides or oligonucleotides hybridize or anneal to different regions of the same linear complementary nucleic acid sequence, and the 3' end of one polynucleotide or oligonucleotide points towards the 5' end of the other, the former may be called the "upstream" polynucletide or oligonucleotide and the latter the "downstream" polynucleotide or oligonucleotide.

A variety of methods are known in the art for making nucleic acids having a particular sequence or that contain particular nucleic acid bases, sugars, internucleoside linkages, chemical moieties, and other compositions and characteristics. Any one or any combination of these methods can be used to make a nucleic acid, polynucleotide, or oligonucleotide for the present invention. Said methods include, but are not limited to: (1) chemical synthesis (usually, but not always, using a nucleic acid synthesizer instrument); (2) post-synthesis chemical modification or derivatization; (3) cloning of a naturally occurring or synthetic nucleic acid in a nucleic acid cloning vector (e.g., see Sambrook, et al., Molecular Cloning: A Laboratory Approach $2^{nd}$ ed., Cold Spring Harbor Laboratory Press, 1989) such as, but not limited to a plasmid, bacteriophage (e.g., m13 or lamba), phagemid, cosmid, fosmid, YAC, or BAC cloning vector, including vectors for producing single-stranded DNA; (4) primer extension using an enzyme with DNA template-dependent DNA polymerase activity, such as, but not limited to, Klenow, T4, T7, rBst, Taq, Tfl, or Tth DNA polymerases, including mutated, truncated (e.g., exo-minus), or chemically-modified forms of such enzymes; (5) PCR (e.g., see Dieffenbach, C. W., and Dveksler, eds., PCR Primer: A Laboratory Manual, 1995, Cold Spring Harbor Laboratory Press, Cold Spring Harbor, N.Y.); (6) reverse transcription (including both isothermal synthesis and RT-PCR) using an enzyme with reverse transcriptase activity, such as, but not limited to, reverse transcriptases derived from avian myeloblasosis virus (AMV), Maloney murine leukemia virus (MMLV), *Bacillis stearothermophilus* (rBst), or *Thermus thermophilus* (Tth); (7) in vitro transcription using an enzyme with RNA polymerase activity, such as, but not limited to, SP6, T3, or T7 RNA polymerase, Tth RNA polymerase, *E. coli* RNA polymerase, or another enzyme; (8) use of restriction enzymes and/or modifying enzymes, including, but not limited to exo- or endonucleases, kinases, ligases, phosphatases, methylases, glycosylases, terminal transferases, including kits containing such modifying enzymes and other reagents for making particular modifications in nucleic acids; (9) use of polynucleotide phosphorylases to make new randomized nucleic acids; (10) compositions, such as, but not limited to, a ribozyme ligase to join RNA molecules; (11) compositions comprising a toposisomerase, or a topoisomerase-DNA intermediate to make chimeric DNA-RNA molecules (International Patent Application No. PCT/US98/12372; International Publication No. WO/98/56943); and/or (12) any combination of any of the above or other techniques known in the art. Oligonucleotides and polynucleotides, including chimeric (i.e., composite) molecules and oligonucleotides with modified bases, sugars, or internucleoside linkages are commercially available (e.g., see the 2000 Product and Service Catalog, TriLink Biotechnologies, San Diego, Calif., USA; www.trilinkbiotech.com).

In General

FIG. 1 shows a schematic representation of a basic embodiment of an analyte-specific assay of the present invention. The embodiment represented in FIG. 1 uses a reporter probe comprising a first portion that is divided into two parts ("Fpa" and "FPb") and a second portion ("SP"), wherein one site on each part of the first portion is joined by a joining method ("JM") to a site on the second portion. The first portion is divided in one of the internal regions that contains major elements of the template recognition site by the replicase (e.g., for MDV-1 RNA, see Nishihara, et al., 1983), to which the second portion can be joined, in order to make a reporter probe that is not replicatable by the replicase. Referring to FIG. 1, the reporter probe is first incubated with a sample or a partially purified fraction of the sample under conditions which permit binding of reporter probe to analyte ("AN"), if present in the sample. In this embodiment, reporter probe molecules that are bound to analyte are then separated from unbound reporter probes. In FIG. 1, the separation is represented as being accomplished by using a capture probe ("CP") that is capable of binding a site on the analyte which is different from the site on the analyte to which the reporter probe binds, and then the capture probe, still bound to analyte to which reporter probe is also bound, is immobilized on a surface by specific binding of a moiety on the capture probe, such as biotin, to a moiety on the surface, such as avidin or streptavidin. The surface is washed to remove unbound reporter probes and reporter probes that are nonspecifically bound. Although this method for separating reporter probe molecules which are bound to analyte from unbound reporter probes comprises one embodiment of the invention, the invention is not limited to use of a capture probe or any particular method of separating reporter probe molecules which are bound to analyte from unbound reporter probes. Also, some embodiments of the invention are homogeneous assays that do not require separation of bound reporter probes from unbound reporter probes. Still referring to FIG. 1, the separated reporter probe molecules which are bound to analyte are then incubated with a nuclease under conditions that bring about the release, liberation, or separation of the parts of the first portion of the reporter probe from the complete reporter probe, which is bound to analyte. Then, the released parts of the first portion of the reporter probe are incubated with a composition having ligase activity, which results in joining of the parts of the first portion. If the parts of the first portion of the reporter probe comprise ribonucleosides (as depicted in FIG. 1), then the ligated first portion can itself be a substrate for replication by a replicase. If the parts comprise deoxyribonucleosides, then an in vitro transcription step is also needed to generate an RNA substrate for replication by a replicase. Once a substrate for replication is generated from the first portion of the reporter probe, the substrate is incubated with the replicase for which the RNA is a substrate under replication conditions. The RNA product that is synthesized is detected by a method known in the art. The invention is not limited by the method used to detect the product. The invention comprises many additional variations and embodiments that will be apparent by examination of the figures and reading of the descriptions, claims, and examples herein.

Replicases of the Invention

A "replicase" according to the invention is an enzyme that catalyzes exponential synthesis (i.e., "replication") of an RNA substrate. The replicase can be from any source for which a suitable exponentially replicatable substrate can be obtained for use in the invention. Preferably, the replicase is an RNA-directed RNA polymerase. In preferred embodiments, the replicase is a bacteriophage replicase, such as Q-beta replicase, MS2 replicase, or SP replicase. In the most preferred embodiment, the replicase is Q-beta replicase. In other preferred embodiments, the replicase is isolated from eucaryotic cells infected with a virus, such as, but not limited to, cells infected with brome mosaic virus, cowpea mosaic virus, cucumber mosaic virus, or polio virus. In another embodiment, the replicase is a DNA-directed RNA polymerase, in which case, a T7-like RNA polymerase (as defined in U.S. Pat. No. 4,952,496) is preferred, and T7 RNA polymerase (Konarska, M. M., and Sharp, P. A., Cell, 63: 609–618, 1990) is most preferred. The replicase can be prepared from cells containing a virus or from cells expressing a gene from a bacteriophage or a eukaryotic virus cloned into a plasmid or other vector.

Replication Reactions

According to the invention, "replication" means synthesis of single-stranded RNA, wherein both the product strand and the template strand from each round of synthesis can be used as a substrate, meaning as a template for synthesis of another complementary single-stranded RNA product, so that, under conditions in which the enzyme is in excess with respect to substrate, the number of RNA strands increases exponentially as the reaction proceeds until the number of RNA substrate molecules exceeds the number of active enzyme molecules in the reaction. Within this definition, it is understood by those with skill in the art that, for a variety of reasons, assays may be suboptimal, so that an actual doubling of RNA substrates may not occur during each round of synthesis. So long as the full-length products of each round of synthesis are capable of being substrates for synthesis in a subsequent round, the synthesis is considered to be exponential synthesis according to the invention. The invention also includes use of enzymes and conditions that result in incorporation of non-canonical nucleotides, including deoxynucleotides and 2'-fluoro and 2'-O-methyl-nucleotides, as substrates (e.g., see Blumenthal, T., and Carmichael, G. G., Ann. Rev. Biochem., 48: 525–548, 1979; U.S. Pat. No. 5,849,546). Therefore, the term "replication" according to the present invention also includes synthesis of products comprising any nucleotides that are substrates for a replicase.

If Q-beta replicase is used, replication of a Q-beta replicase substrate can be carried out substantially according to the protocol of Kramer et al. (J. Mol. Biol., 89: 719–736, 1974). Briefly, an RNA substrate is incubated at 37° C. in a reaction mixture containing about 20–50 micrograms of Q-beta replicase per ml, 40–100 mM Tris-HCl (pH 7–8), about 10–12 mM $MgCl_2$, and about 200–400 micromolar each of ATP, CTP, UTP and GTP. If desired, one of the NTPs can be radioactively labeled with [alpha-$^{32}$P].

If T7 RNA polymerase is used, reaction conditions are similar to those used for in vitro transcription, as described herein. An AMPLISCRIBE T7 High Yield Transcription Kit (Epicentre Technologies, Madison, Wis., USA) is preferred.

Those with skill in the art either know or know how to develop reaction conditions for a particular assay or for other replicases, and will also know that reaction conditions can be changed and empirically evaluated in order to improve yield or some other aspect of an assay. By way of example, but not of limitation, one can modify and evaluate the effects of changing buffer, pH, nucleotide concentration, divalent magnesium cation concentration, salt concentration and ionic strength, quantity of enzyme, temperature, and other variables of a reaction. Under suitable reaction conditions, including the presence of the necessary reagents, the synthesis of RNA will occur. For some embodiments of the invention, modified nucleotides, such as, deoxynucleotides or nucleotides which haver greater resistance to adventitious ribonucleases (e.g., 2'-fluoro- or 2'-O-methyl nucleotides), or which have labels or other properties that are desirable for a particular assay can be used. Also, naturally-occuring or mutant forms of enzymes that can better utilize modified nucleotides, or which have other enzymatic properties can be used. Preferably, replication is carried out in the presence of a suitable ribonuclease inhibitor, chosen from among polyclonal or monoclonal antibody preparations that bind to and inhibit certain adventitious ribonucleases, vanadyl-ribonucleoside complexes, or human placental ribonuclease inhibitor, in order to avoid possible degradation of the RNA product by any adventitious ribonuclease contaminant (e.g., see Sambrook, et al., Chapter 7.4, Molecular Cloning: A Laboratory Approach $2^{nd}$ ed., Cold Spring Harbor Laboratory Press, 1989).

Use of an Exponentially Replicatable RNA and a Replicase as a Signaling System

An important aspect of the invention is that a substrate for replication by a replicase provides a signaling system for the presence of the molecule in which the substrate sequence is embedded or to which it is attached. In preferred embodiments of the invention discussed in greater detail below, the sequence encoded by the first portion of a reporter probe is a signaling system for the second portion or analyte-binding portion of the reporter probe and, indirectly, for the presence of the analyte to which it binds. Most preferably, the signaling system is analyte-specific, meaning it can only be generated if the analyte is present.

Reporter Probes

Another essential aspect of the present invention is a reporter probe having a first portion comprising a polynucleotide that encodes at least part of a substrate for a replicase, and a second portion. The second portion has affinity for the analyte under "binding conditions." The second portion of the reporter probe is joined, linked or attached to the parts of the first portion by a "joining method." The first portion either comprises a polynucleotide that encodes only a part of a substrate for replication by a replicase, wherein the RNA encoded by the part lacks at least one sequence that is required for the RNA to be a substrate, or comprises a polynucleotide that is divided into parts at a site or sites within one or more of the internal regions of the replicase substrate sequence that is required for recognition and binding of the substrate by the replicase enzyme. By way of example, but not of limitation, Nishihara, et al., (J. Biochem., 93: 669–674, 1983) has described major elements of the template recognition region of Q-beta replicase substrates. Those with skill in the art either know or know how to identify sites within this substrate and other substrates where the replicase binds and at which insertion or attachment of an analyte-binding substance results in loss of replicatability of the substrate by the replicase The second portion of the reporter probe can be attached to a part of the first portion at one or more of those sites. Thus, even if the combined parts of the first portion of the reporter probe encode a complete sequence of a substrate for replication, the reporter probe is not a substrate for replication by a replicase. The substrate for replication is formed during the assay by separating the second portion from all of the parts of the first portion and then joining the parts of the first portion in proper sequence using a composition having ligase activity. If the first portion of the reporter probe encodes only part of a sequence of a substrate for replication by a replicase, a substrate which encodes the complete sequence required for replication is formed by ligating one or more nucleotides, including mononucleotides or oligonucleotides, which together encode the missing sequence, to the sequence encoded by the first portion. If the first portion comprises deoxynucleosides, in vitro transcription is also required after joining of the parts of the first portion and one or more mononucleotides or oligonucleotides comprising any missing parts in order to generate a substrate for replication by a replicase.

Configurations of Reporter Probes

Without intending to limit the invention, a reporter probe will usually have one of several general configurations, as shown in FIG. 2. An essential feature of all configurations of the invention is that a reporter probe with a first portion that is joined to a second portion is not a substrate for replication by a replicase of the invention. Because of the activities of replicases like Q-beta replicase discussed in the "Background to the Invention," simple configurations of reporter, such as those having configurations 1 or 2, are not possible if the first portion of the reporter probe encodes a complete substrate for replication by a replicase. Therefore, reporter probes having configuration 1 or 2 generally have a first portion which encodes only a part of the complete sequence for a replicase substrate, which is not replicable by the replicase unless one or more mononucleotides or oligonucleotides encoding the missing sequence is joined or ligated to the released first portion. On the other hand, reporter probes having configurations 3–6 are not substrates for replication by a replicase because the first portions are divided into parts, wherein the sites of division of the parts prevents binding of the separate parts by the replicase. On this basis, configurations of reporter probes of the invention, for which some embodiments are presented in FIG. 2, are briefly described below.

Figure 2A:
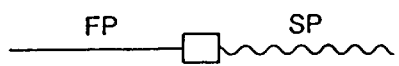
FIG. 2 shows examples of configurations of reporter probes of the invention.

A first configuration of a reporter probe of the invention ("configuration 1") is shown in FIG. 2(a). In configuration 1, the reporter probe is linear in the sense that the second portion of the reporter probe (SP) is joined to the mononucleoside at the most 3'-end of the polynucleotide of the first portion of the reporter probe (FP). For example, if the second portion comprises a polynucleotide, a preferred embodiment of the invention is a reporter probe wherein the most 3'-mononucleoside of the first portion of the reporter probe and the most 5'-mononucleoside of the second portion of the reporter probe are joined by an internucleoside linkage, including, but not limited to, a phosphodiester or a phosphorothioate linkage.

A second configuration of a reporter probe of the invention ("configuration 2") is shown in FIG. 2(b). In configuration 2, the reporter probe is circular in the sense that one site on the second portion of the reporter probe (SP) is joined by a first joining method to the mononucleoside at the most 3'-end of the polynucleotide of the first portion of the reporter probe (FP) and another site on the second portion of the reporter probe is joined by a second joining method to a mononucleoside at the 5'-end of the polynucleotide of the first portion of the reporter probe. The first joining method can be the same or different than the second joining method. As an example of a configuration in which the second portion of the reporter probe comprises a polynucleotide, a preferred embodiment of the invention is a reporter probe wherein an internucleoside linkage, including, but not limited to, a phosphodiester or a phosphorothioate linkage, is used to join both the most 3'-mononucleoside of the first portion of the reporter probe to the most 5'-mononucleoside of the second portion and the most 3'-mononucleoside second portion of the reporter probe to the most 5'-mononucleoside of the first portion.

Figure 2C:
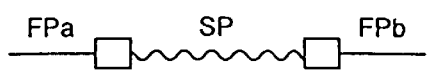

A third configuration of a reporter probe of the invention ("configuration 3") is as depicted in FIG. 2(c). In configuration 3, the polynucleotide of the first portion of the reporter probe is split into two or more parts and each of different sites on the second portion of the reporter probe is joined to one part of the first portion of the reporter probe. For example, for the embodiment in FIG. 2(c), one site on the second portion of the reporter probe is joined by a first joining method to a mononucleoside at the 5'-end or the 3'-end of one part of the first portion of the reporter probe (FPa) and the other site on the second portion of the reporter probe is joined by a second joining method to a mononucleoside at the 3'-end or the 5'-end of the second part of the first portion of the reporter probe (FPb). The first joining method can be the same or different than the second joining method. As an example of configuration 3 in which the second portion of the reporter probe comprises a polynucleotide, a preferred embodiment of the invention is a reporter probe wherein both the first and second joining methods comprise phosphodiester or phosphorothioate internucleoside linkages.

A fourth configuration of a reporter probe of the invention ("configuration 4") is circular, as shown by embodiments in FIGS. 2(d) and 2(e). In the embodiment of a reporter probe of configuration 4 shown in FIG. 2(d), the first and second portions are joined as described for configuration 3. However, in this particular embodiment, the 3'-end of the 3'-part of the first portion (FPb) is additionally joined by a joining method to the 5'-end of the 5'-part of the first portion (FPa) of the reporter probe.

In some embodiments of a reporter probe of the invention, a "linker oligonucleotide," comprising RNA, DNA or both RNA and DNA mononucleotides or modified mononucleotides, is used as part of the joining method. The linker oligonucleotide can serve one or more functions. For example, one purpose for the linker oligonucleotide contemplated by the invention is to serve to hold the two parts of the first portion of the reporter probe in close proximity following their separation from the second portion of the reporter probe by a nuclease. Another purpose for the linker oligonucleotide contemplated for some embodiments of the invention is to serve as a template for ligation of the first part of the first portion of the reporter probe with the second part of the first portion of the reporter probe subsequent to their separation from the second portion of the reporter probe. For example, at least a segment of the linker oligonucleotide can be complementary to both the 3'-end of the 5'-part of the first portion of the reporter probe and the 5'-end of the 3'-part of the first portion of the reporter probe, wherein the 3'-end of the 5'-part is contiguous with the 5'-end of the 3'-part when both parts are hybridized to the linker oligonucleotide. Thus, the linker oligonucleotide serves as a template for ligation of the two parts by a ligase.

For the configuration shown in FIG. 2(d), it should be noted that, even following separation of the second portion from the reporter probe and ligation of the first and second parts of the first portion of the reporter probe, the presence of the linker oligonucleotide still prevents the first portion of the reporter probe from encoding a correct substrate for a replicase. Thus, in those embodiments, additional steps are required to remove the linker and generate a substrate for replication.

In some embodiments of the invention, a "linker mononucleotide" can be used in place of a linker oligonucleotide. By way of example, but not of limitation, deoxyuridine can be used as the linker mononucleotide in the configuration shown in FIG. 2(d), in which case, uracil-N-glycosylase and endonuclease IV can be used as nucleases to separate the two parts of the first portion of the reporter probe.

In another embodiment of a reporter probe of configuration 4, as shown in FIG. 2(e), both the first portion and the second portion are split into parts. In the example shown, each portion is split into two parts, but either or both portions can also be split into more than two parts, with the parts joined by joining method in any order or combination that does not prevent binding of the second portion to the analyte. The different parts of the second portion can bind to different sites on the analyte. By way of example, but not of limitation, for an analyte comprising a nucleic acid, the different parts of a second portion comprising a nucleic acid can bind to different nucleic acid sequences of the analyte, including non-contiguous sequences. The joining method between the parts of the first and second portions can be an internucleoside linkage, such as, but not limited to, a phosphodiester or phosphorothioate linkage, or it can be a linker mononucleotide or a linker oligonucleotide, as discussed above.

Configuration 5 of a reporter probe of the invention is linear, as shown by embodiments in FIGS. 2(f) and 2(g). In configuration 5, both the first portion and the second portion of the reporter probe comprise two or more parts. In these examples, both portions comprise two parts. In the embodiment of configuration 5 shown in FIG. 2(f), the two parts of the first portion of the reporter probe are joined to each other, with the most 3'-mononucleoside of the most 3'-part of the first portion of the reporter probe (FPb) being joined by a first joining method to the most 5'-mononucleoside of the most 5'-part of the first portion (FPa). This first joining method comprises a linker mononucleotide or a linker oligonucleotide, as described above, which is joined in a typical 5'-to-3' orientation to each of the two parts of the first portion by an internucleoside linkage, such as, but not limited to, a phosphodiester or a phosphorothioate linkage. The 3'-end of the most 5'-part of the first portion of the reporter probe (FPa) is joined by a second joining method to the first part of the second portion of the reporter probe (SPa), and the 5'-end of the most 3'-part of the first portion of the reporter probe (FPb) is joined by a third joining method to the second part of the second portion of the reporter probe (SPb). If the second portion of the reporter probe comprises a polynucleotide, one embodiment, for example, comprises a polynucleotide in which the 3'-end of the most 3'-part of the second portion (SPb) is joined to the 5'-end of the most 3'-part of the first portion of the reporter probe (FPb) and the 3'-end of the most 5'-part of the first portion (FPa) is joined to the 5'-end of the most 5'-part of the second portion (SPa). The joinings can be by an internucleoside linkage, such as, but not limited to, a phosphodiester or a phosphorothioate linkage. Both the 5'-end of the most 3'-part of the second portion (SPb) and the 3'-end of the most 5'-part of the second portion (SPa) of the reporter probe are free (i.e., unjoined).

In another embodiment of configuration 5 shown in FIG. 2(g), the two parts of the first portion of the reporter probe are not joined to each other. In this particular example, assuming the second portion comprises a nucleic acid that is complementary to a nucleic acid analyte, the 3'-ends of both parts of the first portion are joined to the 5'-ends of parts of the second portion, and the 3'-end of one part of the second portion is joined to the 5'-end of a part of the first portion (it could be either part, but is shown in FIG. 2(g) as the first part of the first portion). The 5'-end of one part of the first portion of the reporter probe, and the 3'-end of one part of the second portion are free (i.e., unjoined). The joining methods between the parts of the first and second portions can be an internucleoside linkage, such as, but not limited to, a phosphodiester or phosphorothioate linkage, or it can be a linker mononucleotide or a linker oligonucleotide, as discussed above.

In some embodiments of configuration 5, the parts of the second portion of the reporter probe are designed so that they are not contiguous when hybridized to a nucleic acid analyte to which they are complementary. By way of example, but not of limitation, the reporter probes of configuration 5 shown in FIGS. 2(f) and 2(g) can have a second portion comprising two parts that hybridize to non-contiguous sequences in the target analyte.

Configuration 6 of reporter probes of the invention also comprises first and second portions which are each split into two or more parts. However, in configuration 6, the reporter probe also comprises two or more molecules. In the embodiment of configuration 6 depicted in FIG. 2(h), the reporter probe comprises two molecules, but the reporter probe can also comprise more than two molecules, each with two or more parts. In the embodiment depicted, the reporter probe comprises a first and a second molecule, wherein the first molecule comprises a first part of the first portion of the reporter probe (FPa) which is joined to a site on one part of the second portion (e.g., SPa) and the second molecule comprises a second part of the first portion of the reporter probe (FPb) which is joined to a site on the second part of the second portion (e.g., SPb).

Superficially, reporter probes of the present invention, especially those of configuration 6 resemble the binary probes described by researchers such as Tyagi, et al. (e.g., see U.S. Pat. No. 5,759,773), Martinelli, et al. (U.S. Pat. No. 5,959,095), or by Chu, et al. (U.S. Pat. Nos. 5,631,129) for Q-beta replicase. However, reporter probes of configuration 6 of the present invention have important differences compared to the binary probes for Q-beta replicase described by those researchers. Most importantly, the substrates for replication by a replicase of the present invention do not contain an analyte-binding substance (e.g., targe-complementary sequence). In contrast, the replicatable substrates described by other researchers such as Tyagi, et al., Martinelli, et al., and Chu, et al. all contained target-complementary sequences in addition to Q-beta MDV sequences. This difference in the substrate for replication results from a distinguishing feature of the methods and assays of the present invention. Whereas researchers such as Tyagi, et al., Martinelli, et al., Chu, et al., and others (Landegren, U., et al., Science, 241: 1077–1080, 1988 and Science, 242: 229–237, 1988; Epicentre Technologies, "AMPLIGASE Thermostable DNA Ligase," 1989; Wu, D. Y., and Wallace, B., Genomics, 4: 560–569, 1989; Nickerson, D., et al., Proc. Natl. Acad. Sci. USA, 87: 8923–8927, 1990; U.S. Pat. Nos. 5,494,810; 5,506,137; 5,679,524; 5,686,243; 5,800,994; 5,830,711; 5,854,033; 5,912,148; 6,054,564) have used target-dependent ligation of probes and amplification of the target sequence in order to detect the presence of the target in a sample, the assays of the present invention use ligation only as a method to generate a substrate for replication by a replicase. Replication of the substrate serves as a signaling system for the presence of the analyte, but no target-complementary sequence is ligated or replicated with the probe. When an assay of the present invention requires the target to be present in order to generate a signal, this target dependence is needed in order to generate a substrate for a composition with nuclease activity, such as, but not limited to, an RNase H. The nuclease digests the second portion or analyte-binding portion of the reporter probe and releases the parts of the first portion of the reporter probe so they can be ligated to form a replicatable substrate for a replicase.

The invention also covers other configurations of reporter probes than those described above. For example, it is obvious to those with skill in the art that although configurations are described above as having the first portion and second portions divided into no more than two parts, the invention also includes configurations in which the first portion, the second portion, or both first and second portions are divided into two or more parts which are joined in various orders or combinations by joining method. Also, some embodiments of the invention comprise two or more reporter probes having certain of the above-described configurations that are joined in tandem or in series. Reporter probes that are joined in series can be the same or they can be different from each other. If different reporter probes are joined in series, with each reporter probe having a second portion with affinity for a different analyte, the serially joined reporter molecules can be used in assays for detecting multiple analytes, such as multiplex assays. The invention also comprises certain embodiments in which circular molecules are formed by joining the free ends of a series of two or more serially joined reporter probes, whether said reporter probes are the same or different.

The invention also comprises reporter probes, wherein the second portion of the reporter probe comprises an analyte-binding substance that is not a polynucleotide. The invention includes all of the configurations of such reporter probes, whether the joining method is the same or different from the joining methods described as examples above. Joining methods of the invention are described more fully in the section below entitled "Joining Methods of Reporter Probes." The invention is not limited by the joining method used, and configurations of reporter probes with other joining methods are also included in the invention.

The First Portion (FP) of the Reporter Probe

The first portion of a reporter probe of the invention comprises a single-stranded polynucleotide that encodes at least part of a sequence of a substrate for a replicase. The first portion of the reporter probe comprises a polynucleotide comprising DNA, RNA, or both DNA and RNA mononucleotides, whether unmodified or modified mononucleotides, which modifications can be in the nucleic acid bases, in the sugar moieties, or in the internucleoside linkages.

Substrates for Replication by a Replicase

The invention contemplates that various substrates for replication can be used in the invention based on the replicase used. The invention is not limited by the replication substrate used. Any RNA that is a substrate for a particular replicase can be used in an assay of the invention. Preferred replicases of the invention are Q-beta replicase and T7 RNA polymerase. In embodiments that use Q-beta replicase, it is preferred that the sequence of the recombinant template be derived from the sequence of an RNA in the following group: midivariant RNA (MDV-1 RNA), microvariant RNA, nanovariant RNA, CT RNA, RQ135 RNA, RQ120 RNA, other variants not yet named, and Q-beta RNA. In embodiments that use T7 RNA polymerase, a preferred substrate is X RNA or Y RNA (Konarska, M. M., and Sharp, P. A., Cell, 63: 609–618, 1990). Either the plus or the minus strand of an RNA substrate can be used. Also, substrates derived from known substrates, such as substrates that are mutated or modified to contain a feature, such as, but not limited to, a restriction site, can be used. DNA shuffling techniques, such as those developed by Willem Stemmer at Maxygen (U.S. Pat. Nos. 5,605,793; 5,811,238; 5,830,721), can be used to make a new substrate that comprises parts of other substrates.

If a suitable substrate is not known or is not available for use in an assay of the invention for a particular replicase, a new substrate can be prepared. By way of example, but not of limitation, new candidate RNA substrates for replication by a replicase can be generated by incubating a random RNA copolymer, such as poly(A,U,I,C) or poly (A,U,G,C), comprising a large number of different RNA strands, with the replicase in a reaction mixture containing a 0.5–10 mM each of ATP, UTP, CTP, and GTP or ITP, 0.1–20 mM of a divalent magnesium or manganese salt, and other reaction conditions that are suitable for the enzyme. It is also desirable to use a small amount of a radioactive nucleoside triphosphate, such as about $10^6$ cpm of tritium-labeled UTP as a way to measure RNA synthesis by incorporation into a polynucleotide product. Following incubation at a suitable temperature under suitable conditions, an aliquot of the reaction mixture is analyzed for radioactive UTP incorporation by precipitation using cold 5% trichloroacetic acid, and assaying for radioactivity incorporated using a scintillation counter. Another aliquot is transferred to a fresh reaction mixture, incubated in the presence of the replicase, and then again analyzed for UTP incorporation. Serial transfers are repeated until incorporation of label reaches a maximum.

Random RNA copolymers for use in generating new RNA substrates for replication can be prepared by a variety of methods known in the art. For example, the method of Biebricher and Orgel (Proc. Nat. Acad. Sci. USA, 70: 934–938, 1973) can be used. These researchers generated poly(A,U,I,C) copolymers enzymatically using polynucleotide phosphorylase. Alternatively, random RNA copolymers can be synthesized using commercially available oligonucleotide synthesizers. Random DNA copolymers can also be synthesized using an oligonucleotide synthesizer and then cloned into a vector downstream from a phage T7, T3, or SP6 RNA polymerase promoter. Random RNA can then be synthesized by in vitro transcription. Also, random RNA can be synthesized using a method called "SELEX," as described in U.S. Pat. No. 5,270,163 and related patents. Other methods for generating random copolymers are apparent to those knowledgeable in the art, and are included in the present invention.

Once a substrate for a replicase is identified, improved substrates can be obtained by serial transfer and selection of higher yielding products from successive reactions, including prolonged reactions, using methods similar to those described above to find the original substrate. Further, improved substrates can be obtained by random or site-directed modification of a known substrate, followed by use of methods similar to those used to select new substrates that result in greater incorporation of UTP during replication.

Reporter Probes Having A First Portion (FP) Comprising RNA Mononucleotides

In embodiments of the invention in which the first portion of the reporter probe comprises RNA mononucleosides, any polynucleotide comprising a single-stranded RNA that is a substrate for a replicase, as discussed above, can be used. In preferred embodiments, the first portion of the reporter probe comprises an RNA that is a substrate for Q-beta replicase or T7 RNA polymerase. In one preferred embodiment which uses Q-beta replicase, the substrate is a midivariant RNA, but other substrates can also be used. In another preferred embodiment which uses T7 RNA polymerase, the substrate comprises one of the strands of X RNA or Y RNA. The polynucleotide of the first portion of the reporter probe can comprises RNA mononucleotides chosen from among both unmodified mononucleotides and modified mononucleotides which confer a benefit, such as phosphorothioate linkages which are more resistant to adventitious nucleases. As discussed in the section entitled "Reporter Probes," the first portion is divided into parts and joined to the second portion so as to make the reporter probe unreplicatable by the replicase.

Once a substrate for replication by a replicase is chosen for use in an assay, a polynucleotide encoding either a part of the substrate is used in a first portion of the reporter probe (e.g., for configurations 1 and 2), or the first portion comprises separate parts which, together, encode the complete sequence for the substrate (e.g., configurations 3–6). In both cases, it is important that, for the polynucleotide that encodes the part of the substrate used in the first portion does not render the reporter probe replicable by the replicase. In order to decrease the probability of a substrate being generated during an assay which is not related to the presence of an analyte (i.e., a false positive assay result), it is desirable that: (1) the first portion of the reporter probe comprises a polynucleotide that encodes a part of the substrate which is less likely to be replicable unless it is ligated to an oligonucleotide that encodes the missing part of the substrate; or (2) the first portion comprises a polynucleotide that encodes the complete sequence, but the first portion is divided into parts at a site or sites that are known to be important for replication. For example, insertions made in MDV-1 (+) RNA between nucleotides 63 and 64 do not greatly alter the replicability of the substrate by Q-beta replicase (e.g., see U.S. Pat. No. 4,786,600), so dividing this substrate into parts at this site is not preferred in the methods of the invention. On the other hand, 40 of 46 nucleotides between positions 81 and 126 of MDV-1 (+) RNA are identical with nucleotides 84 to 129 of Q-beta (−) RNA and 30 of 35 nucleotides between positions 187 and 221 at the 3'-end of MDV-1 (+) RNA are identical with nucleotides 4186 to 4220 at the 3'-end of Q-beta (−) RNA (Nishihara, T., et al., J. Biochem., 93: 669–674, 1983). These regions contain major elements of the internal replicase binding site and the product strand intiation site. Thus, by way of example, but not of limitation, it is preferred, according to the present invention, that a first portion of a reporter probe that encodes MDV-1 (+) RNA is divided into parts within one of these regions which is known to be required for replication. Most preferably, a first portion of a reporter probe that encodes MDV-1 (+) RNA is divided into parts within a region of the sequence that is required for binding of the replicase, such as, but not limited to, in the region between nucleotides 81 and 126 of MDV-1 (+) RNA. Similarly, if other polynucleotides that encode other substrates are used in the first portion of a reporter probe of the invention, it is preferred that the sequence of the polynucleotide that comprises the first portion is divided into parts within a region that is required for replication. Also, if a polynucleotide that encodes only part of a sequence for a substrate is used for the first portion of the reporter probe, it is preferred that the sequence of the polynucleotide used either starts or terminates within a region that is required for replication by the replicase; preferably, the polynucleotide of the first portion lacks a sequence that is necessary to bind the replicase. This strategy is in contrast to the strategy of most other scientists who have used Q-beta replicase substrates for analyte-specific assays. Most other scientists, including those who have used Q-beta binary probes (e.g., U.S. Pat. Nos. 5,631, 129; 5,759,773; 5,959,095 and European Patent No. EP0519053B1), have intentionally avoided attaching an analyte-specific sequence within a region that is important for replication. This is an important difference between the present invention and the prior art, which results in reduced background in assays of the present invention.

Reporter Probes Having A First Portion (FP) Comprising DNA Mononucleotides

In one embodiment of the invention, the first portion of the reporter probe comprises DNA mononucleotides, chosen from among both unmodified mononucleosides and modified mononucleosides which confer a benefit, such as those having phosphorothioate internucleoside linkages, which are more resistant to nucleases.

Once a suitable RNA substrate for an assay of the invention has been identified, as described above, there are a variety of methods known in the art to generate DNA that corresponds to the RNA for use in a first portion of a reporter probe comprising DNA mononucleosides. For example, the RNA can be sequenced using methods known in the art for RNA sequencing (e.g., see Konarska and Sharp, Cell, 63: 609–618, 1990). Alternatively, the RNA can be reverse transcribed by methods known in the art for using an enzyme with reverse transcriptase activity, and then, the cDNA can be cloned into a vector and sequenced. Once the RNA sequence is known, a corresponding cDNA strand which has a single-stranded RNA polymerase promoter sequence attached to the 3'-end can be synthesized using an oligonucleotide synthesizer. Formation of a double-stranded promoter by annealing a complementary oligodeoxynucleotide to the promoter sequence of the first portion permits in vitro transcription by an RNA polymerase that recognizes the promoter. Alternatively, in some embodiments, the promoter sequence can be a hairpin structure at the 3'-end of the sequence of the replicase substrate, the stem of which comprises a double-stranded promoter, thus eliminating the requirement that a separate complementary DNA strand be present to hybridize to the sequence encoding the promoter to form a functional promoter. The hairpin is either on the most 3'-part of the first portion of the reporter probe or at the 3'-end of an oligonucleotide that is ligated to the first portion following its release from the reporter probe. Many other methods for making a reporter probe having a first portion comprising DNA mononucleosides or modified mononucleosides are apparent to those knowledgeable in the art, and are also included in the invention.

In one embodiment of the invention, the first portion of the reporter probe is a polynucleotide comprising a single-stranded DNA that encodes part of an RNA that is a substrate for a replicase and a single-stranded promoter sequence for an RNA polymerase. In a preferred embodiment, the first portion of the reporter probe comprises single-stranded DNA that encodes RNA that is a substrate for Q-beta replicase and a single-stranded promoter sequence for an RNA polymerase. In one preferred embodiment, the first portion of a reporter probe of the invention comprises single-stranded DNA that encodes at least part of one of the strands of MDV-1 and a single-stranded promoter sequence chosen from among promoter sequences for SP6, T3, and T7 RNA polymerases. In another preferred embodiment, the first portion of a reporter probe of the invention comprises single-stranded DNA that encodes at least part of one of the strands of X RNA or Y RNA and a single-stranded promoter sequence chosen from among promoter sequences for SP6, T3, and T7 RNA polymerases. In other preferred embodiments, the RNA polymerase promoter sequence is on the 3'-end of an oligonucleotide that encodes the missing sequence of the replicase substrate, which missing sequence is ligated to the first portion of the reporter probe following release of the first portion from the reporter probe in an assay of the invention. A promoter sequence is attached, joined, linked or appended to the 3'-end of the most 3'-part of the polynucleotide that encodes a complete substrate for replication by a replicase, which promoter sequence can be on the first portion of the reporter probe or at the 3'-end of an oligonucleotide that encodes the missing sequence of the replicase substrate, either as a single-stranded sequence to which another promoter complementary oligonucleotide must be annealed, or as a double-stranded hairpin structure.

Promoter Sequences for Use In Transcribing First Portions of Reporter Probes Comprising DNA Mononucleotides The promoter sequence used in the first portion of a reporter probe comprising DNA mononucleosides can be any RNA polymerase promoter sequence that is recognized specifically by a DNA-dependent RNA, such as, but not limited to, those described by Chamberlin and Ryan (In: The Enzymes. San Diego, Calif., Academic Press, 15: 87–108, 1982) and by Jorgensen, et al., (J. Biol. Chem., 266: 645–655,1991). Several RNA polymerase promoter sequences are preferred: these include, but are not limited to, promoters derived from SP6 (e.g., Zhou, and Doetsch, Proc. Nat. Acad. Sci. USA, 90: 6601–6605, 1993), T7 (e.g., Martin, and Coleman, Biochemistry, 26: 2690–2696, 1987) and T3 (e.g., McGraw, et al., Nucl. Acid. Res., 13: 6753–6766, 1985). An RNA polymerase promoter sequence derived from Thermus thermophilus (e.g., Wendt, et al., Eur. J. Biochem., 191: 467–472, 1990; Faraldo, et al., J. Bact., 174: 7458–7462, 1992; Hartmann, et al., Biochem, 69: 1097–1104, 1987; Hartmann, et al., Nucl. Acids Res., 19: 5957–5964, 1991) can also be used. The length of the promoter sequence will vary depending upon the promoter chosen. For example, the T7 RNA polymerase promoter can be only about 25 bases or less in length to act as functional promoter, while other promoter sequences require 50 or more bases to provide a functional promoter.

The Second Portion (SP) or Analyte-Binding Portion of the Reporter Probe

Another essential aspect of a reporter probe of the invention is that the reporter probe, in addition to the first portion, also has a second portion (SP) or analyte-binding portion which is joined to the first portion. The second portion of the reporter probe has affinity for and "binds" to the analyte under "binding conditions."

The composition of the second portion of the reporter probe can vary for different analytes. The "analyte-binding portion" comprises an "analyte-binding substance," an "affinity molecule," an "affinity substance," a "specific binding substance," or a "binding molecule," for the analyte. Analyte-binding substances for particular analytes and methods of preparing them are well known in the art.

A preferred analyte-binding substance for the second portion of a reporter probe of the invention is a nucleic acid or a polynucleotide or an oligonucleotide or a segment of a nucleic acid or polynucleotide, including nucleic acids composed of DNA, RNA, or both DNA and RNA mononucleosides, including modified DNA or RNA mononucleosides. When an analyte-binding substance comprising a nucleic acid is used in the second portion of the reporter probe, a preferred analyte of the invention is a nucleic acid, polynucleotide or oligonucleotide which has a segment or region that is at least partially complementary with at least a segment or region of the analyte-binding substance. Such nucleic acid affinity molecules can be made by any of numerous known in vivo or in vitro techniques, including, by way of example, but not of limitation, automated nucleic acid synthesis techniques, PCR, or in vitro transcription. As understood in the art, the length that a DNA or RNA affinity molecule must have to provide a pre-determined specificity in an assay will depend in part on the amount and complexity of nucleic acid in the sample being assayed. Such an affinity molecule will usually require at least five nucleotides.

An analyte-binding substance which is a nucleic acid, polynucleotide, oligonucleotide or a segment of a nucleic acid or polynucleotide, including nucleic acids composed of either DNA or RNA, or both DNA and RNA mononucleosides, including modified DNA or RNA mononucleosides, can also be used according to the invention in the second portion of a reporter probe for an analyte that does not comprise nucleic acid. For example, a method termed "SELEX," as described by Gold and Tuerk in U.S. Pat. No. 5,270,163, can be used to select a nucleic acid for use as an analyte-binding substance according to the invention. SELEX permits selection of a nucleic acid molecule that has high affinity for a specific analyte from a large population of nucleic acid molecules, at least a portion of which have a randomized sequence. For example, a population of all possible randomized 25-mer oligonucleotides (i.e., having each of four possible nucleic acid bases at every position) will contain $4^{25}$ (or $10^{15}$) different nucleic acid molecules, each of which has a different three-dimensional structure and different analyte binding properties. SELEX can be used, according to the methods described in U.S. Pat. Nos. 5,270,163; 5,567,588; 5,580,737; 5,587,468; 5,683,867; 5,696,249; 5723,594; 5,773,598; 5,817,785; 5,861,254; 5,958,691; 5,998,142; 6,001,577; 6,013,443; and 6,030,776, incorporated herein by reference, in order to select an analyte-binding nucleic acid with high affinity for a specific analyte that is not a nucleic acid or polynucleotide for use in the second portion of the reporter probe. Once selected using SELEX, nucleic acid affinity molecules can be made by any of numerous known in vivo or in vitro techniques, including, by way of example, but not of limitation, automated nucleic acid synthesis techniques, PCR, or in vitro transcription.

Naturally occurring nucleic acid or polynucleotide sequences that have affinity for other naturally occurring molecules such as, but not limited to, protein molecules, are also known in the art. Examples include, but are not limited to certain nucleic acid sequences such as operators, promoters, origins of replication, sequences recognized by steroid hormone-receptor complexes, restriction endonuclease recognition sequences, ribosomal nucleic acids, and so on, which are known to bind tightly to certain proteins. For example, in two well-known systems, the lac repressor and the bacteriophage lambda repressor each bind to their respective specific nucleic acid sequences called "operators" to block initiation of transcription of their corresponding mRNA molecules. Nucleic acids containing such specific sequences can be used in the invention as analyte-binding substances for the respective proteins or other molecules for which the nucleic acid has affinity. In these cases, the nucleic acid with the specific sequence is used as the analyte-binding substance of the second portion of the reporter probe in assays for the respective specific protein, glycoprotein, lipoprotein, small molecule or other analyte that it binds. One of several techniques which are generally called "footprinting" (e.g., see Galas, D. and Schmitz, A, Nucleic Acids Res., 5: 3161, 1978) can be used to identify sequences of nucleic acids which bind to a protein. Other methods are also known to those with skill in the art and can be used to identify nucleic acid sequences for use as specific analyte-binding substances for use in the invention.

A "peptide nucleic acid (PNA)" or a molecule comprising both a nucleic acid and a PNA, as described in U.S Pat. Nos. 5,539,082; 5,641,625; 5,700,922; 5,705,333; 5,714,331; 5,719,262; 5,736,336; 5,773,571; 5,786,461; 5,817,811; 5,977,296; 5,986,053; 6,015,887; and 6,020,126 (and references therein), can also be used according to the invention as an analyte-binding substance for an analyte that is a nucleic acid or polynucleotide. In general, a PNA molecule is a nucleic acid analog consisting of a backbone comprising, for example, N-(2-aminoethyl)glycine units, to each of which a nucleic acid base is linked through a suitable linker, such as, but not limited to an aza, amido, ureido, or methylene carbonyl linker. The nucleic acid bases in PNA molecules bind complementary single-stranded DNA or RNA according to Watson-Crick base-pairing rules. However, the $T_m$'s for PNA/DNA or PNA/RNA duplexes or hybrids are higher than the $T_m$'s for DNA/DNA, DNA/RNA, or RNA/RNA duplexes. Thus, use of PNA as an analyte-binding substance in the second portion of a reporter probe of the invention provides tighter binding (and greater binding stability) in assays for a nucleic acid analyte (e.g., see U.S. Pat. No. 5,985,563). Also, since PNA is not naturally occurring, PNA molecules are highly resistant to protease and nuclease activity. PNA for use as an analyte binding substance in the second portion of reporter probes of the invention can be prepared according to methods know in the art, such as, but not limited to, methods described in the above-mentioned patents, and references therein. Antibodies to PNA/DNA or PNA/RNA complexes can be used in the invention for capture, recognition, detection, identification, or quantitation of nucleic acids in biological samples, via their ability to bind specifically to the respective complexes without binding the individual molecules (U.S. Pat. No. 5,612,458).

The invention also contemplates that a combinatorial library of randomized peptide nucleic acids prepared by a method such as, but not limited to, the methods described in U.S. Pat. Nos. 5,539,083; 5,831,014; and 5,864,010, can be used to prepare analyte-binding substances for the second portion of the reporter probe for use in assays for analytes of all types, including analytes that are nucleic acids, proteins, or other analytes, without limit. As is the case for the SELEX method with nucleic acids, randomized peptide or peptide nucleic acid libraries are made to contain molecules with a very large number of different binding affinities for an analyte. After selection of an appropriate affinity molecule for an analyte from a library, the selected affinity molecule can be used in the invention as an analyte-binding substance in the second portion of the reporter probe.

An analyte-binding substance can also be an oligonucleotide or polynucleotide with a modified backbone that is not an amino acid, such as, but not limited to modified oligonucleotides described in U.S. Pat. Nos. 5,602,240; 6,610,289; 5,696,253; or 6,013,785.

The invention also contemplates that an analyte-binding substance can be prepared from a combinatorial library of randomized peptides (i.e., comprising at least four naturally-occurring amino acids). One way to prepare the randomized peptide library is to place a randomized DNA sequence, prepared as for SELEX, downstream of a phage T7 RNA polymerase promoter, or a similar promoter, and then use a method such as, but not limited to, coupled transcription-translation, as described in U.S. Pat. Nos. 5,324,637; 5,492,817; or 5,665,563, or stepwise transcription, followed by translation. Alternatively, a randomized DNA sequence, prepared as for SELEX, can be cloned into a site in a DNA vector that, once inserted, encodes a recombinant MDV-1 RNA containing the randomized sequence that is replicatable by Q-beta replicase (e.g., between nucleotides 63 and 64 in MDV-1 (+) RNA; see U.S. Pat. No. 5,620,870). The recombinant MDV-1 DNA containing the randomized DNA sequence is downstream from a T7 RNA polymerase promoter or a similar promoter in the DNA vector. Then, following transcription, the recombinant MDV- 1 RNA, containing the randomized sequence can be used to make a randomized peptide library comprising at least four naturally-occurring amino acids by coupled replication-translation as described in U.S. Pat. No. 5,556,769. An analyte-binding substance can be selected from the library by binding peptides in the library to an analyte, separating the unbound peptides, and identifying one or more peptides that is bound to analyte by means known in the art. Alternatively, high throughput screening methods can be used to screen all individual peptides in the library to identify those which can be used as analyte-binding substances. Although the identification of an analyte-binding peptide by these methods is difficult and tedious, the methods in the art are improving for doing so, and the expenditure of time and effort required may be warranted for identifying analyte-binding substances for use in assays of the invention that will be used routinely in large numbers.

A variety of other analyte-binding substances can also be used in the second portion of reporter probes of the invention.

For an antigen analyte (which itself may be an antibody), antibodies, including monoclonal antibodies, are available as analyte-binding substances. For certain antibody analytes in samples which include only one antibody, an antibody binding protein such as Staphylococcus aureus Protein A can be employed as an analyte-binding substance.

For an analyte, such as a glycoprotein or class of glycoproteins, or a polysaccharide or class of polysaccharides, which is distinguished from other substances in a sample by having a carbohydrate moiety which is bound specifically by a lectin, a suitable analyte-binding substance is the lectin.

For an analyte which is a hormone, a receptor for the hormone can be employed as an analyte-binding substance. Conversely, for an analyte which is a receptor for a hormone, the hormone can be employed as the analyte-binding substance.

For an analyte which is an enzyme, an inhibitor of the enzyme can be employed as an analyte-binding substance. For an analyte which is an inhibitor of an enzyme, the enzyme can be employed as the analyte-binding substance.

Usually, an analyte molecule and an affinity molecule for the analyte molecule are related as a specific "binding pair", i.e., their interaction is only through non-covalent bonds such as hydrogen-bonding, hydrophobic interactions (including stacking of aromatic molecules), van der Waals forces, and salt bridges. Without being bound by theory, it is believed in the art that these kinds of non-covalent bonds result in binding, in part due to complementary shapes or structures of the molecules involved in the binding pair.

The term "binding" according to the invention refers to the interaction between an analyte-binding substance or affinity molecule and an analyte as a result of non-covalent bonds, such as, but not limited to, hydrogen bonds, hydrophobic interactions, van der Waals bonds, and ionic bonds.

Based on the definition for "binding," and the wide variety of affinity molecules and analytes which can be used in the invention, it is clear that "binding conditions" vary for different specific binding pairs. Those skilled in the art can easily determine conditions whereby, in a sample, binding occurs between affinity molecule and analyte that may be present. In particular, those skilled in the art can easily determine conditions whereby binding between affinity molecule and analyte, that would be considered in the art to be "specific binding," can be made to occur. As understood in the art, such specificity is usually due to the higher affinity of affinity molecule for analyte than for other substances and components (e.g., vessel walls, solid supports) in a sample. In certain cases, the specificity might also involve, or might be due to, a significantly more rapid association of affinity molecule with analyte than with other substances and components in a sample.

"Hybridization" is the term used to refer to the process of incubating an affinity molecule comprising a nucleic acid, or a peptide nucleic acid (PNA) molecule, or a covalently linked, joined or attached nucleic acid-PNA molecule with an analyte comprising a nucleic acid under "binding conditions," which are also called "hybridization conditions." The ability of two polymers of nucleic acid containing complementary sequences to find each other and anneal through base pairing interaction is a well-recognized phenomenon. The initial observations of the "hybridization" process by Marmur and Lane (Proc. Nat. Acad. Sci. USA, 46: 453, 1960) and Doty, et al. (Proc. Nat. Acad. Sci. USA, 46: 461, 1960) have been followed by the refinement of this process into an essential tool of modern biology. "Hybridization" also refers to the "binding" or "pairing" of complementary nucleic acid bases in a single-stranded nucleic acid, PNA, or linked nucleic acid-PNA affinity molecule with a single-stranded nucleic acid analyte, which occurs according to base pairing rules (e.g., adenine pairs with thymine or uracil and guanine pairs with cytosine). Those with skill in the art will be able to develop and make conditions which comprise binding conditions or hybridization conditions for particular nucleic acid analytes and reporter probes of an assay. In developing and making binding conditions for particular nucleic acid analytes and reporter probes, as well as in developing and making hybridization conditions for particular analytes and capture probes, certain additives can be added in the hybridization solution. By way of example, but not of limitation, dextran sulfate or polyethylene glycol can be added to accelerate the rate of hybridization (e.g., Chapter 9, Sambrook, et al., Molecular Cloning: A Laboratory Manual, $2^{nd}$ Edition, Cold Spring Harbor Laboratory Press, 1989), or betaine can be added to the hybridization solution to eliminate the dependence of $T_m$ on basepair composition (Rees, W. A., et al., Biochemistry, 32, 137–144, 1993).

The terms "degree of homology" or "degree of complementarity" are used to refer to the extent or frequency at which the nucleic acid bases on one strand (e.g., of the affinity molecule) are "complementary with" or "able to pair" with the nucleic acid bases on the other strand (e.g., the analyte). Complementarity may be "partial," meaning only some of the nucleic acid bases are matched according to base pairing rules, or complementarity may be "complete" or "total." The length (i.e., the number of nucleic acid bases comprising the nucleic acid and/or PNA affinity molecule and the nucleic acid analyte), and the degree of "homology" or "complementarity" between the affinity molecule and the analyte have significant effects on the efficiency and strength of binding or hybridization when the nucleic acid bases on the affinity molecule are maximally "bound" or "hybridized" to the nucleic acid bases on the analyte. The terms "melting temperature" or "$T_m$" are used as an indication of the degree of complementarity. The $T_m$ is the temperature at which a population of double-stranded nucleic acid molecules becomes half dissociated into single strands under defined conditions. Based on the assumption that a nucleic acid molecule that is used in hybridization will be approximately completely homologous or complementary to a target polynucleotide, equations have been developed for estimating the $T_m$ for a given single-stranded sequence that is hybridized or "annealed" to a complementary sequence. For example, a common equation used in the art for oligodeoxynucleotides is: $T_m = 81.5°$ C.$+0.41$ (%G+C) when the nucleic acid is in an aqueous solution containing 1 M NaCl (see e.g., Anderson and Young, Quantitative Filter Hybridization, in Nucleic Acid Hybridization, 1985). Other more sophisticated equations available for nucleic acids take nearest neighbor and other structural effects into account for calculation of the $T_m$. Binding is generally stronger for PNA affinity molecules than for nucleic acid affinity molecules. For example the $T_m$ of 10-mer homothymidine PNA binding to its complementary 10-mer homoadenosine DNA is 73° C., whereas the $T_m$ for the corresponding 10-mer homothymidine DNA to the same complementary 10-mer homoadenosine DNA is only 23° C. Equations for calculating the $T_m$ for a nucleic acid are not appropriate for PNA. Preferably, a $T_m$ that is calculated using an equation in the art, is checked empirically and the hybridization or binding conditions are adjusted by empirically raising or lowering the stringency of hybridization as appropriate for a particular assay. As used herein the term "stringency" is used in reference to the conditions of temperature, ionic strength, and the presence of other compounds, under which nucleic acid hybridizations are conducted. With "high stringency" conditions, nucleic acid base pairing will occur only between nucleic acid fragments that have a high frequency of complementary base sequences. Thus, conditions of "weak" or "low" stringency are often required when it is desired that nucleic acids that are not completely complementary to one another be hybridized or annealed together.

With regard to complementarity, it is important for some assays of the invention to determine whether the hybridization represents complete or partial complementarity. For example, where it is desired to detect simply the presence or absence of pathogen DNA (such as from a virus, bacterium, fungi, mycoplasma, protozoan), it is only important that the hybridization method ensures hybridization when the relevant sequence is present. In those embodiments of the invention, conditions can be selected where both partially complementary probes and completely complementary probes will hybridize.

However, the invention can also be used for assays to detect mutations, or genetic polymorphisms, or single nucleotide polymorphisms (SNPs). These embodiments of the invention require that the hybridization and other aspects of the method distinguish between partial and complete complementarity. For example, human hemoglobin is composed, in part, of four polypeptide chains. Two of these chains are identical chains of 141 amino acids (alpha chains) and two of these chains are identical chains of 146 amino acids (beta chains). The gene encoding the beta chain is known to exhibit polymorphism. The normal allele encodes a beta chain having glutamic acid at the sixth position. The mutant allele encodes a beta chain having valine at the sixth position. This difference in amino acids has a profound (most profound when the individual is homozygous for the mutant allele) physiological impact known clinically as sickle cell anemia. It is well known that the genetic basis of the amino acid change involves a single base difference between the normal allele DNA sequence and the mutant allele DNA sequence. Thus, some embodiments of the invention are used for assays that can detect and distinguish even as small a difference as a single basepair in a nucleic acid analyte.

Joining Methods for Reporter Probes

A joining method is used to join, link or attach the parts of the second portion of the reporter probe to the parts of the first portion of the reporter probe. The invention comprises different joining methods depending on the compositions of the first and second portions of the reporter probe and other factors.

As discussed above in the section entitled "First Portion of the Reporter Probe," the first portion of a reporter probe of the invention is always a nucleic acid or polynucleotide. If the second portion of a reporter probe also comprises a nucleic acid or polynucleotide, then a preferred joining method comprises an internucleoside linkage, such as, but not limited to, a phosphodiester or phosphorothioate linkage between the first portion and the second portion. In some embodiments of the invention, a preferred joining method comprises a mononucleotide or an oligonucleotide comprising RNA, DNA, or both RNA and DNA mononucleosides or modified mononucleosides, wherein said mononucleotide or oligonucleotide is in turn joined to the first and second portions of the reporter probe by internucleoside linkages, such as, but not limited to, phosphodiester or phosphorothioate linkages. Appropriate joining methods for a particular embodiment are determined by considering a number of factors, including, but not limited to, the configuration of the reporter probe, the composition of the first portion, the composition of the second portion, the nuclease used to release the parts of the first portion, and other factors.

If the second portion of the reporter probe does not comprise a nucleic acid or polynucleotide, then a preferred joining method of the invention comprises an "oligonucleotide linker" comprising RNA, DNA, or both RNA and DNA mononucleosides which are joined to the first portion of the reporter probe by at least one internucleoside linkage, such as, but not limited to, a phosphodiester or phosphorothioate linkage, and to the second portion of the reporter probe by any method which does not interfere with the ability of analyte-binding substance of the second portion to bind to its analyte under binding conditions. The oligonucleotide linker can be joined to the analyte-binding substance of the second portion of the reporter probe by a covalent chemical linkage or by a non-covalent linkage, such as, but not limited to, the linkage formed between biotin and streptavidin. The joining of the first portion of the reporter probe to the second portion through an oligonucleotide linker provides a stable joining method that permits predictable, controlled release of the first portion, as discussed below. In some embodiments, a mononucleotide linker can be used as a joining method.

The composition of the second portion of a reporter probe and the joining method may vary for different reporter probes and different analytes. Since the nature and composition of the joining method affects the nature and composition of the release method, joining methods of the invention will be more fully understood from by the description of release methods in the section below entitled "Release Methods."

Evaluation and Modification of Reporter Probes

Prior to use in an assay of the invention, each reporter probe is evaluated in various ways in order to judge its suitability for the assay. By way of example, but not of limitation, each reporter probe is incubated under conditions for replication by the replicase in order to assure that no signal is generated in the absence of analyte or in the absence of a nuclease to release the parts of the first portion and a ligase to generate a substrate for replication. If the various tests performed indicate that there is a problem or a potential problem, experiments are performed to identify the cause or causes of the problem and possible solutions, which are also evaluated.

Still by way of example, but not of limitation, one problem that can be envisioned for a reporter probe comprising a second portion comprising nucleic acid is that the reporter probe is replicated by the replicase. This situation would cause problems of background in an assay. One possible solution for this potential problem is to try to join the second portion a different site in the first portion of the reporter probe (i.e., to divide the first portion into different parts and join the second portion to different sites in the first portion). The invention contemplates that it should be possible to find a site or sites within the substrate for replication that will prevent binding to and replication of the substrate by the replicase. Thus, if a reporter probe is a substrate for the replicase, one or more new reporter probes is made which have one or more parts of the second portion joined to different sites of the first portion. These new reporter probes are evaluated and modifications made until the problem is solved. Other potential problems, if any, are also evaluated and analyzed in a similar empirical manner, and modifications to the reporter probes are made which hopefully resolve the problem or potential problem.

Release Methods

One or more nucleases or other compositions is used in a "release method" or "liberation method" in the present invention to "release" or "liberate" the parts of the first portion of a reporter probe that encode a substrate for replication by a replicase.

The invention is not limited by the release method used. The release method of the invention varies depending on a number of factors, including, but not limited to, the nature and composition of the target analyte, the configuration of the reporter probe, the composition of the first portion of the reporter probe, the composition of the second portion of the reporter probe, and the method or methods of joining the first and second portions. The release method can comprise one composition and step, or it can constitute multiple compositions and steps.

If the first portion of the reporter probe comprises DNA or RNA mononucleosides, the release method can comprise contacting the reporter probe which is bound to an analyte, said analyte comprising a nucleic acid, with a nuclease that digests only the second portion of the reporter probe or that separates the second portion from the parts of the first portion. Any nuclease that results in digestion of the second portion or its separation from the parts of the first can be used.

If the analyte does not comprise a nucleic acid, it is preferred that the first portion of the reporter probe is linked to the second portion using an oligonucleotide linker, as discussed above in the section entitled "Joining Methods for Reporter Probes." In embodiments that use such an oligonucleotide linker, preferred embodiments use a nuclease that digests the oligonucleotide linker so as to release the parts of the first portion of the reporter probe from the analyte-binding substance of the second portion.

In preferred embodiments of the invention, the release or liberation of an RNA that is a substrate for replication by a replicase depends on, requires, or occurs only in the presence of analyte in the sample. However, the invention is not limited to release methods or liberation methods that occur only in the presence of analyte. If the release or liberation of an RNA substrate for replication does not require the presence of analyte in the sample, then the assay must be designed so as to assure that all reporter probe molecules which are not bound to an analyte are separated from reporter probe molecules which are bound to the analyte prior to treating bound reporter probe molecules with the release method.

The most preferred embodiments use a release method that requires the presence of analyte. For example, if the analyte is a polynucleotide comprising deoxynucleotides (i.e., DNA) and the second portion of the reporter molecule comprises an oligoribonucleotide (i.e., RNA) that is complementary to at least a portion of the analyte, then release or liberation of the RNA encoded by the first portion of the reporter probe by an enzyme with ribonuclease H (RNase H) activity is dependent upon the presence of the analyte in the sample. That is, a RNase H is active in digesting the phosphodiester bonds of the second portion of the reporter probe if and only if the second portion is hybridized (i.e., is bound) to the analyte (e.g., see Donis-Keller, Nucl. Acids Res., 7: 179–192, 1979). Since the release method in the latter example is active only in the presence of the analyte, the likelihood for nonspecific release of reporter probe molecules that are not bound to analyte is reduced.

The invention also contemplates that more than one release method can be used, which release methods can be the same or different from each other. If different release methods are used, each release method can have different characteristics. By way of example, but not of limitation, one release method can depend on the presence of analyte in the sample, while the other does not.

Table 1 below identifies examples, but not limitations, of some, but not all, of the situations covered by the invention. The designations "FP" and "SP" refer to the first portion and second portion, respectively, of the reporter probe. Additional situations are also discussed in the specifications.

TABLE 1

| | | Reporter Probe | |
|---|---|---|---|
| Situation | Analyte | FP | SP |
| I | DNA | RNA | RNA |
| II | DNA | RNA | RNA + DNA |
| III | DNA | RNA | RNA + PNA |
| IV | Non-NA* | RNA | RNA-L** + ABS*** |
| V | DNA | DNA | RNA |
| VI | DNA | DNA | RNA + DNA |
| VII | DNA | DNA | RNA & PNA |
| VIII | DNA | RNA | DNA |
| IX | DNA | DNA | DNA |
| X | DNA | RNA | DNA & PNA |
| XI | DNA | DNA | DNA & PNA |
| XII | RNA | RNA | RNA |
| XIII | RNA | RNA | DNA |
| XIV | RNA | DNA | RNA |
| XV | RNA | DNA | DNA |
| XVI | RNA | RNA | RNA & PNA |
| XVII | RNA | RNA | DNA & PNA |
| XIX | RNA | DNA | RNA & PNA |
| XX | RNA | DNA | DNA & PNA |
| XXI | Non-NA* | DNA | DNA-L** + ABS*** |

*Non-NA = An analyte that is not nucleic acid
**RNA-L = RNA Linker; DNA-L = DNA Linker
***ABS = Analyte-Binding Substance The following release methods illustrate, but are not intended to limit the invention with respect to the variety of ways by which the part of the first portion of a reporter probe can be released from the second portion in a reporter probe or reporter probe-analyte hybrid (i.e., a "bound" reporter probe). The situations are designated by roman numerals that refer to the situations in Table 1.

1. Use of Ribonuclease H (RNase H) in Release Methods.

Assays which use RNase H as a release method are most preferred embodiments of the invention. "Ribonuclease H" or "RNase H" according to the invention is an enzyme that digests RNA that is hybridized to DNA but that does not digest unhybridized RNA. An RNase H of the invention is not limited by its source. By way of example, but not of limitation, the RNase H can be derived from *Escherichia* coli, or it can be from a thermophilic source, such as the enzymes from *Thermus thermophilus* and *Thermus flavus* described in U.S. Pat. Nos. 5,268,289; 5,459,055; and 5,500,370. The RNase H can be purified from a natural source, such as, but not limited to a bacterium or a bacteriophage source, or it can be from a recombinant source. An enzyme which has RNase H activity in addition to other activities, such as DNA-dependent or RNA-dependent (i.e., reverse transcriptase) DNA polymerase activity, or another enzymatic activity, can be used as an RNase H in an assay of the invention under appropriate conditions. Whether the enzyme is suitable for use in a release method in an assay can be determined simply by testing it by methods well known in the art. In order to use RNase H in a release method in assays of the invention, each region of the reporter probe which is desired to be digested using RNase H will comprise at least one monoribonucleotide, and usually, at least three consecutive monoribonucleotides.

While not wishing to be bound by any particular theory, it is believed that certain criteria must be met for RNase H to recognize and elicit cleavage of an RNA strand. The first of these is that the RNA strand at the cleavage site must have its nucleosides connected via an internucleoside linkage that bears a negative charge. Additionally, the sugar of the nucleosides of the DNA strand at the cleavage site must be a .beta.-pentofuranosyl sugar and also must be in a 2' endo conformation. The only nucleosides (nucleotides) that fit this criteria are phosphodiester, phosphorothioate, phosphorodithioate, phosphoroselenate and phosphorodiselenate nucleotides of 2'-deoxy-erythro-pentofuranosyl .beta.-nucleosides.

In view of the above criteria, even certain nucleosides on the DNA strand that have been shown to reside in a 2' endo conformation (e.g., cyclopentyl nucleosides) will not elicit RNase H activity since they do not incorporate a pentofuranosyl sugar. Modeling has shown that oligonucleotide 4'-thionucleosides also will not elicit RNase H activity, even though such nucleosides reside in an envelope conformation, since they do not reside in a 2' endo conformation. Additionally, since .alpha.-nucleosides are of the opposite configuration from .beta.-pentofuranosyl sugars they also will not elicit RNase H activity.

The invention is not limited to RNase H enzymes that require the above structural criteria to cleave an RNA that is hybridized to a DNA, and other enzymes with RNase H activity that have other criteria for cleavage can also be used in assays of the invention.

RNase H is a most preferred release method if the analyte comprises DNA mononucleosides and both first and second portions of the reporter probe comprise RNA mononucleosides joined by an internucleoside linkage such as, but not limited to a phosphodiester or phosphorothioate linkage (situations I-IV).

If the first portion of the reporter probe comprises an RNA polynucleotide that is a substrate for replication by a replicase, then contacting the reporter probe bound to analyte with RNase H under release conditions comprises a most preferred release method (situation I).

Situations II-IV illustrate the use of reporter probes in which the second portion is of mixed composition. There are various reasons why it is desirable to use a reporter probe that has a second portion of mixed composition in assays of the invention. By way of example, but not of limitation, one reason is to localize the nucleosides that are acted upon by the release method to a certain region or regions of the second portion of the reporter probe. For example, for a release method which comprises contacting bound reporter probes with RNase H, if the RNA mononucleotides that are digested by RNase H are localized in only the regions that are joined by joining method to the first portion of the reporter probe and the remaining region of the second portion comprises, for example, DNA or PNA, then the probability is increased that the release of the first portion by release method will be successful. This is because, if the RNase H had first digested ribonucleotide bonds that were not adjacent to the ribonucleotides of the first portion, then the second portion may not remain annealed to the analyte for a long enough time to permit release of a first portion that lacks ribonucleotides of the second portion (i.e., RNase H digestion is not complete). Since the ribonucleotides of the second portion must be digested from or separated from the parts of the first portion in order for the first portion of the reporter probe to be a substrate for replication by a replicase, incomplete digestion by RNase H in the presence of analyte may result in a decrease in the sensitivity of the assay, or, if the quantity of analyte approaches the limit of detection, a false negative assay outcome. Another reason to use a reporter probe that has a second portion of mixed composition is to use one composition to increase the binding affinity of the second portion to the analyte, while using the other composition to retain the ability to use a desirable release method. For example, a composition comprising PNA has a higher binding affinity for a DNA analyte than RNA, but a composition comprising RNA permits use of a release method comprising RNase H, which is preferred. Therefore, a second portion comprising both RNA, which is joined to the first portion of the reporter probe, and PNA is a preferred composition for some embodiments of the invention.

The composition of the second portion of the reporter probe can also be important for performance of certain methods or applications of the invention. By way of example, but not of limitation, one embodiment of the invention uses a reporter probe comprising a second portion of mixed composition for a method to detect mutations, including, but not limited to, single base mutations or single nucleotide polymorphisms ("SNPs"). This can be accomplished, for example, by designing the reporter probe so that the second portion of the reporter probe comprises a sequence that is complementary to the sequence in the analyte in which the mutation or SNP occurs, if present, such that a ribonucleotide that is complementary to the nucleotide of the mutation or SNP in the analyte is immediately adjacent to and joined by joining method, such as, but not limited to, a phosphodiester linkage, to the first portion of the reporter probe. Thus, the mutation or SNP will be detected if the first portion is released from or separated from the second portion by digestion of the joining method at the ribonucleotide that is complementary to the mutated nucleotide or SNP by a release method, such as contacting the bound reporter probe with RNase H. As a control for the assay, another reporter probe is also used which comprises a second portion with the same sequence except that a ribonucleotide complementary to the "wild type" nucleotide or SNP is joined immediately adjacent to the first portion of the reporter probe. The first portion of the control reporter probe would be released in the presence of RNase H if the analyte contains the wild-type sequence but would not be released if the analyte only contains the mutated nucleotide or SNP. As described previously, each region of the reporter probe which is subject to digestion using RNase H as a release method comprises at least one monoribonucleotide, and usually, at least three consecutive monoribonucleotides, including the ribonucleotide which is complementary to the respective wild type or mutant nucleotide or SNP. The remaining region of the second portion of reporter probes of these embodiments of the invention can comprise PNA, DNA, or both PNA and DNA. The use of a peptide nucleic acid increases the binding affinity of the macromolecule to the complementary strand of the analyte nucleic acid. PNA and, to a lesser extent, DNA also make the reporter probe more resistant to degradation by cellular nucleases. In embodiments of the invention that use reporter probes to assay for nucleotide mutations or SNPs, it is also beneficial to use a second portion of mixed composition (i.e., RNA adjacent to the first portion and PNA or DNA elsewhere in the second portion of the reporter probe) in order to localize the ribonucleotide regions which are subject to digestion when using RNase H as a release method, as discussed above.

In situation IV, the analyte is not a nucleic acid. The analyte-binding substance (ABS) can comprise a nucleic acid, whether DNA or RNA, such as, but not limited to a nucleic acid that is selected using SELEX (as described in U.S. Pat. No. 5,270,163 and related patents described in the section entitled "The Second Portion (SP) or Analyte-Binding Portion of the Reporter Probe"), or which contains a naturally-occurring sequence that binds to the analyte, or that is obtained or selected by another method. Alternatively, the analyte binding substance of the second portion of the reporter probe can comprise a peptide, a protein, a lectin, or another analyte-binding substance, such as those discussed in the section entitled "The Second Portion (SP) or Analyte-Binding Portion of the Reporter Probe." In general, whether the analyte-binding substance is a nucleic acid or another analyte-binding substance, it will be joined to at least one mononucleotide or oligonucleotide linker, each of which will in turn be joined to at least a part of the first portion of the reporter probe through an internucleoside linkage such as, but not limited to, a phosphodiester linkage. If the analyte-binding substance is a nucleic acid or polynucleotide, it will be joined to the mononucleotide or oligonucleotide linker through an internucleoside linkage such as, but not limited to, a phosphodiester linkage. If the analyte-binding substance is a peptide, protein, or another non-nucleic acid analyte-binding substance, it will preferably be linked to the linker through a chemical bond that is stable under all conditions used in the assay. Preferably the chemical bond is a covalent bond. A variety of methods for making such chemical linkages between various analyte-binding substance and a mononucleotide of a linker, including those comprising modified nucleosides, are well known in the art. Less preferably, the chemical linkage is a non-covalent bond, such as, but not limited to the bond between biotin and avidin or streptavidin. The invention is not limited by the method of chemical linkage, except that the linkage should be stable under all of the conditions used in the assay and it should not affect the ability of the analyte-binding substance to bind the analyte under binding conditions. In embodiments of the invention for situation IV, oligonucleotide linkers comprising monoribonucleosides are preferred and the preferred release method comprises annealing to each oligonucleotide linker an oligonucleotide comprising at least a DNA segment that is complementary to the linker and contacting the bound reporter probe to which the DNA-containing oligonucleotide is hybridized with RNase H. In addition to being complementary to the linker, the complementary DNA-containing oligonucleotide can, but need not, have at least a part that comprises PNA or RNA (but not DNA) and that is complementary to at least a part of the first portion of the reporter probe, so as to increase the efficiency of annealing to the reporter probe and the release of the first portion.

As discussed above, embodiments that use a reporter probe with a second portion comprising at least a segment comprising RNA mononucleotides and RNase H as at least part of the release method are preferred embodiments of the present invention. Therefore, for target analytes comprising ribonucleic acid, the invention includes embodiments in which ribonucleic acid analytes in a sample are reverse transcribed using an enzyme with reverse transcriptase activity, such as, but not limited to, MMLV reverse transcriptase or rBst or Tth DNA polymerase (available from Epicentre Technologies, Madison, Wis., USA), and either specific oligodeoxynucleotide primers or random primers, such as, random hexamer primers or oligo(dT)18 primers, according to procedures that are well-known in the art, in order to generate a cDNA target nucleic acid. Generation of cDNA target nucleic acids from ribonucleic acid in samples permits use of preferred embodiments of reporter probes and release methods of the invention.

In situations V-VII, RNase H can be used to release the parts of the first portion of the reporter probe by digestion of at least a segment of the second portion which comprises RNA mononucleosides which are joined to a part of the first portion by an internucleoside linkage, such as a phosphodiester or phosphorothioate linkage.

2. Use of a 5' Nuclease as a Release Method.

Another release method according to the present invention uses a 5' nuclease or CLEAVASE enzyme as a "cleavage method" as described by Kwiatkowski, et al. (Molecular Diagnosis, 4: 353–364, 1999) and in U.S. Pat. No. 6,001,567 and related patents assigned to Third Wave Technologies, Madison, Wis., USA, which are incorporated herein by reference.

The 5' nucleases that can be used in the present invention are structure-specific enzymes that are essential for DNA replication, recombination, and repair, as reviewed by Lieber (Bioessays, 19:233–240, 1997). "Structure-specific nucleases" or "structure-specific enzymes" are enzymes that recognize specific secondary structures in a nucleic acid molecule and cleave these structures (i.e., "cleavage structures"). The 5' nucleases comprise a "cleavage method" (i.e., they cleave a nucleic acid molecule in response to the formation of a cleavage structure. The cleavage structure is a substrate for specific cleavage by said cleavage method in contrast to a nucleic acid molecule that is a substrate for non-specific cleavage by agents, such as phosphodiesterases, that cleave nucleic acid molecules without regard to secondary structure (i.e., no formation of a duplexed structure is required). The products generated by the reaction of a cleavage method with a cleavage structure are referred to as "cleavage products."

The present invention is not limited to use of particular enzymes described herein, and other enzymes with similar activities can also be used. However, a 5' nuclease that can be used as a release method or part of a release method of the present invention usually comprises an enzyme in one of two classes. The first class consists of enzymes derived from the 5' exonuclease domains of DNA polymerase I (i.e., "Pol I-type") enzymes, especially from thermophilic eubacteria (Lyamichev, V., et al., Science, 260: 778–783, 1993). When a 5' nuclease activity is associated with a Pol I-type DNA polymerase (DNAP), it is found in the one-third N-terminal region of the protein as an independent functional domain. Gelfand et al. (WO 92/06200) showed that the 5' exonuclease activity usually associated with DNAPs is a structure-dependent single-stranded endonuclease and is more properly referred to as a 5' nuclease. Cleavase enzymes of the Pol I-type have been engineered to eliminate their polymerase activity. Thus, the 5' nucleases of this class can be native Pol I-type DNAPs, or they can be derived from Pol I-type DNAPs that retain 5' nuclease activity but have reduced or absent synthetic activity. The second class includes flap endonucleases ("FEN-1"), as are isolated from thermophilic archaebacteria, that do not have an associated DNA polymerase activity(Harrington, J. J., and Lieber, M. R., EMBO J., 13: 1235–1246, 1994).

Thus, the cleavage method can include 5' nuclease activity provided from a variety of sources including, but not limited to, the CLEAVASE enzymes (Third Wave Technologies, Madison, Wis., USA), the FEN-1 endonucleases (including AfuFEN, PfuFEN, MjaFEN, and Mth-FEN proteins), Tth DNA polymerase, Taq DNA polymerase and *E. coli* DNA polymerase I. The cleavage method can be a "thermostable" enzyme, by which is meant an enzyme that is functional or active (i.e., can perform catalysis) at an elevated temperature, i.e., at about 55° C. or higher.

In order to use a 5' nuclease as a release method in methods of the present invention, a reporter probe is used as a "probe oligonucleotide," as defined by Kwiatkowski, et al. (Molecular Diagnosis, 4: 353–364, 1999). That is, a reporter probe that is bound or annealed to a target analyte that comprises a nucleic acid (DNA or RNA) interacts with the target nucleic acid to form a cleavage structure in the presence or absence of an invader oligonucleotide. The second portion of the reporter probe anneals to the target and the first portion of the reporter probe is similar to the "flap" of the probe oligonucleotides described by Kwiatkowski, et al. The preferred cleavage site by these 5' nucleases is a phosphodiester bond in the double helical region between displaced single-stranded DNA and "invaded" double-helical DNA.

An "invader oligonucleotide" is as defined by Kwiatkowski, et al. (Molecular Diagnosis, 4: 353–364, 1999). With respect to the present invention, the invader oligonucleotide forms a cleavage structure by hybridizing to a target nucleic acid upstream of the site on the target to which the reporter probe is hybridized, which reporter probe is then cleaved by the 5' nuclease. The presence of the upstream invader oligonucleotide greatly stimulates cleavage by the 5' nucleases when its 3'-end overlaps or "invades" the duplex formed by the downstream second portion of the reporter probe and the target nucleic acid by at least one nucleotide (Lyamichev, V., et al., Nature Biotechnol., 17: 292–296, 1999; Proc. Nat. Acad. Sci. USA, 96: 6143–6148, 1999; and Kaiser, M. W., et al., J. Biol. Chem., 274: 21387–21394,1999). Thus, by way of example, but not of limitation, an invader oligonucleotide can be designed for the present invention to have one base of invasion, meaning that, when both the invader oligonucleotide and the reporter probe are hybridized to the analyte, the 3'-end of the invader oligonucleotide extends into or "invades" the analyte-binding substance (i.e., the target-complementary region) of the second portion of the reporter probe by one base. Although at least one base of invasion by the 3'-end of the invader oligonucleotide is required for cleavage, the identity of that 3' terminal base of the invader oligonucleotide is not important, and it need not be complementary to the target (Kwiatkowski, R. W., et al., Molecular Diagnosis, 4: 353–364, 1999). In the case of the one base of invasion just discussed, the preferred cleavage site of the 5' nuclease on the reporter probe is at the 3'-side of the invaded base. Thus, in some embodiments, a reporter probe can be designed so that the 5' nuclease cleaves the reporter probe that is bound or hybridized to analyte so that a substrate for replication is generated [i.e., the first portion of the reporter probe is released in a target-specific manner, but (like the "flap" described below for INVADER Squared assays) is a non-target cleavage product of the reaction].

The reporter probe of the present invention, including the parts of the first and second portions, is designed so as to have a cleavage site which results in release of the parts of the first portion of the reporter. An invader oligonucleotide can be used in embodiments of the present invention that use a 5' nuclease as a cleavage method, but it is not required so long as a cleavage structure is formed such that a 5' nuclease cleaves the first portion of the reporter probe from the reporter probe. That is, other methods of forming a cleavage structure without using an invader oligonucleotide can also be used.

The use of a 5' nuclease as part of a release method in assays of the invention is a preferred method only for certain configurations of reporter probes, such as some embodiments of configuration 4. A 5' nuclease is not preferred for configurations of reporter probes in which a part of the first portion of the reporter probe is not always 5' of the second portion or a part of the second portion. If a configuration of a reporter probe is used which has more than one joining site between the first portion and the second portion of the reporter probe, those with skill in the art will understand that a 5' nuclease can only be used in a similar way to cleave the first portion or part of the first portion of the reporter probe from the reporter probe if said first portion is 5' of the sequence of the analyte-binding second portion. By way of example, but not of limitation, an invader oligonucleotide can be designed so that a 5' nuclease will cleave a circular reporter probe having configuration 2 at the 5'-end of the second portion of the reporter probe, resulting in a free 3'-end for the first portion of the reporter probe. However, an invader oligonucleotide could not be designed in a similar way to cause contemporaneous cleavage of the 3'-end of the second portion of the reporter probe from the 5'-end of first portion; therefore, another method needs to be used to cleave the reporter probe at this site. Another release method, in addition to the use of a 5' nuclease, can be used to cleave at other joining sites; however, embodiments that use the minimum number of release methods are usually preferred.

The invention also includes multiplex assays, by which is meant simultaneous assays for multiple analytes in the same reaction. Those with skill in the art will understand that multiple invader oligonucleotides can be used with a 5' nuclease in such assays as part of the release method for multiple reporter probes having configuration 4. In some assays of the invention, an invader oligonucleotide can be used in common in the release method for different target nucleic acids, while in other assays, different invader oligonucleotides are used for different target nucleic acids. By way of example, but not of limitation, a single invader oligonucleotide and a single 5' nuclease can sometimes be used with different reporter probes to detect different "SNPs" or single nucleotide polymorphisms (i.e., having different nucleic acid bases at a particular position) in a nucleic acid sequence which is otherwise identical or nearly identical.

The target nucleic acids and types of probes for which a 5' nuclease can be used in a release method of the present invention are as described by Kwiatkowski, et al. (Molecular Diagnosis, 4: 353–364, 1999) and in U.S. Pat. No. 6,001,567 and related patents. According to those descriptions, an invader oligonucleotide and a 5' nuclease can be used for target nucleic acids comprising DNA or RNA, and for probes that comprise DNA, RNA or both DNA and RNA. Therefore, an invader oligonucleotide and a 5' nuclease can be used as a release method for any of the situations listed in Table I.

Without being bound by theory, the inventor believes that, when the sequence of the target analyte permits design of a reporter probe that will generate a substrate for replication by a replicase by cleavage with a 5' nuclease, assays of the present invention for detecting nucleic acid sequences, mutations, and SNPs that use a 5' nuclease as a release method can be more sensitive than current assays using invader oligonucleotides and a 5' nuclease, including those referred to as "INVADER Squared" assays. In the latter "Invader Squared" assays (see Kwiatkowski, et al., Molecular Diagnosis, 4: 353–364, 1999, and references therein), in the presence of a target sequence, an oligonucleotide fragment (i.e., a "flap" or "non-target cleavage product") that results from cleavage of a target-specific probe (such as a "Mut Probe" or a "WT Probe") in the presence of a first Invader Oligo and a 5' nuclease becomes a second Invader Oligo for a signal probe called a "FRET Probe." The present invention includes use of invader oligonucleotides and 5' nucleases, as described by Kwiatkowski, et al. (Molecular Diagnosis, 4: 353–364, 1999) and in U.S. Pat. Nos. 6,001,567 and related patents, as a release method for the present invention. Further, the use of the methods and compositions of the present invention to improve the sensitivity and other features of the various embodiments of "Invader" or "Cleavase" assays are included within the methods and claims of the present invention.

In using an invader oligonucleotide and a 5' nuclease as a release method, care must be taken to assure that the 5' nuclease does not cleave the RNA products during replication. If the 5' nuclease recognizes the structure formed during replication as a cleavage structure, then the assay must include steps to inhibit, inactivate, or remove the 5' nuclease prior to replication. By way of example, but not of limitation, an inhibitor of the 5' nuclease that comprises DNA or RNA can be obtained using SELEX, in a manner similar to that described for obtaining an inhibitor for Taq and Tth DNA polymerases (U.S. Pat. No. 6,020,130). Alternatively, a polyclonal or monoclonal antibody that binds to and inhibits the active site of the 5' nuclease can be prepared and used for this purpose. Also, the assays can employ alternative 5' nucleases that are easily inactivated because, for example, they are thermolabile or require different reaction conditions for activity; such enzymes can be obtained from natural sources (e.g., from a psychrophilic or extremophilic organism), or by mutation of genes for 5' nucleases that have already been purified. Still further, the RNA released in an assay from the first portion of the reporter probe can be purified away from the 5' nuclease by a variety of means, such as, but not limited to, selective precipitation of the RNA and or nucleic acid in the reaction, or binding or extraction of the protein. Still further, by way of example, but not of limitation, the released RNA can be bound (e.g., by hybridization) to an oligonucleotide attached to a surface, washed to remove the nuclease, and then denatured into a reaction mixture for replication.

3. Other Release Methods.

A number of other compositions and methods exist that can be used as a release method of the invention, and the invention is not limited by the release method used. Careful consideration of the nature and composition of the target analyte, the configuration of the reporter probe, the composition of the first portion of the reporter probe, the composition of the second portion of the reporter probe, and the method of joining the first and second portions will enable those with knowledge in the art to choose an appropriate release method for a particular assay.

Without limiting the invention, the examples given below illustrate compositions for use as release method. In some cases, modified nucleotides might be needed or beneficial to obtain the desired specificity of release.

1. Site-specific cleavage with uracil-N-glycosylase (UNG) and endonuclease IV (endo IV) for a reporter probe which is designed to have a 2'-deoxyuridine moiety at a specific cleavage site or sites. UNG hydrolyzes the N-glycosidic bond between the deoxyribose sugar and uracil in single- and double-stranded DNA that contains uracil in place of thymidine. It has no activity on RNA or dUMP. Endo IV cleaves the phosphodiester linkage at the abasic site. It may be useful to use a thermolabile UNG (e.g., HK-UNG from Epicentre Technologies, Madison, Wis., USA) for some applications. The BESS-T Excision Enzyme Mix (Epicentre Technologies), containing both HK-UNG and Endo IV, can be used.

2. Site-specific cleavage of a reporter probe bound to analyte using a "nucleic acid repair enzyme" as defined in U.S. Pat. No. 5,763,178, and related patents and patent applications assigned to Trevigen, Inc., Gaithersburg, Md., USA. Said enzymes include, but are not limited to, enzymes in the endonuclease III family, including nucleic acid glycosylases and other mismatch repair enzymes, including enzymes from both non-thermophilic and thermophilic sources. A nucleic acid repair enzyme that is used in an embodiment of the present invention can be made up of two separate enzymes, with one enzyme having glycosylase activity and the other having AP (i.e., apurininc/apyrimidinic) cleaving activity, or the nucleic acid repair enzyme can have only glycosylase activity, in which case a separate enzyme with AP cleaving activity is also used. Using nucleic acid repair enzymes as a release method in the present invention, reporter probes can be designed for release of the first portion from reporter probes that are bound to an analyte in an analyte-dependent manner, which is a preferred embodiment of the invention. Also, as discussed above with respect to using a 5' nuclease as a release method, the use of certain nucleic acid repair enzymes as a release method according to the present invention enables design of reporter probes that can detect a single base mutation or a single nucleotide polymorphism (SNP). By way of example, but not of limitation, this can be accomplished by designing the reporter probe to detect a mutation by incorporating a base which is complementary to the wild type base but mismatched with respect to the mutant base at a site on second portion of the reporter probe adjacent to the first portion. Then, a nucleic acid repair enzyme that cleaves at the specific mismatch will separate the first portion of the reporter probe from the second portion as part of the release method.

3. Cleavage of a reporter probe, at least a portion of which comprises ribonucleosides, with a single-strand-specific ribonuclease (such as ribonuclease A or ribonuclease T1).

4. Site-specific cleavage of an RNA reporter probe or an RNA encoded by a DNA reporter probe with a ribozyme. A ribozyme can be designed to cleave a particular site in the RNA. By way of example, but not of limitation, some embodiments of reporter probes of the present invention can incorporate a ribozyme in ways similar to those described by Stefano for MDV-1 probes in U.S. Pat. Nos. 5,472,840 and 5,763,171.

5. Site-specific cleavage of an RNA reporter probe with ribonuclease III ("RNase III"). RNase III only cleaves double-stranded RNA at particular sequences (Krinke, L., and Wulff, D. L., Nucl. Acids Res., 18: 4809–4815,1990). However, itwill cleave almost all double-stranded RNAs if they are sufficiently long. For this reason, it is not preferred.

6. Site-specific cleavage of a reporter probe with a restriction endonuclease. The invention includes, but is not limited to, use of restriction enzymes, like FokI, that cut at a site different than its recognition sequence (Szybalski, W., Gene, 40: 169–173, 1985).

7. Use of exonuclease III (exo III) to digest a second portion comprising DNA that is annealed to a DNA analyte. Exo III digests duplex DNA in a 3'-to-5' direction. The fact that it has low activity on phosphorothioate internucleoside linkages can be used to advantage in designing reporter probes of the invention that use exo III as a release method.

Ligation of the Parts of the First Portion of a Reporter Probe

Following release of the first portion of the reporter probe, a polynucleotide that encodes a complete sequence for a substrate for replication by a replicase must be generated. Therefore, if the first portion of a reporter probe comprises only part of a sequence for a substrate (e.g., configurations 1 and 2), or a complete sequence that is divided into two or more parts (e.g., configurations 3–6), then a polynucleotide that encodes a substrate for replication by a replicase is generated using a "joining method" or "ligation method." Preferably, the ligation method comprises an enzyme that has activity as a ligase, meaning an enzyme that ligates the 3'-end of a 5'-part of the first portion of the reporter probe with the 5'-end of the next downstream or 3'-part of the first portion, and at least one "ligation template." A ligation template is complementary to nucleic acid bases of the 3'-end of the 5'-part and nucleic acid bases of the 5'-end of the 3'-part, such that, when the two parts are annealed to the ligation template, the 3'-end of the 5'-part is adjacent to the 5'-end of the next downstream 3'-part so as to form a "ligation junction." In some embodiments of the invention, the ligation template can be a sequence in the reporter probe, such as a "linker oligonucleotide" used for joining the parts, as discussed in the section entitled "Configurations of Reporter Probes." Since most substrates for replication are at least partially palindromic, the ligation template can also be internal to the first portion of the reporter probe, especially if, for example, two parts of the first portion are designed so as to be asymmetrical in length. Alternatively, a "ligation oligonucleotide," meaning a separate oligonucleotide that is not joined to the reporter probe and which has a sequence that can serve as a ligation template, can be used. Following liberation of the parts of the first portion of the reporter probe by a release method such as, but not limited to, ribonuclease H (as discussed above), the parts of the first portion (and oligonucleotides comprising any missing parts) are allowed to anneal to one or more ligation templates. Then, the 3'-end of a 5'-part is ligated to the 5'-end of a 3'-part using a composition with joining or ligase activity. The invention is not limited by the composition used so long as the enzyme used is active in joining or ligating the parts. If the parts of the first portion of the reporter probe comprise RNA mononucleosides, T4 RNA ligase, T4 DNA ligase, a ribozyme ligase (e.g., U.S. Pat. No. 5,652,107), or another composition having ligase activity can be used. T4 DNA ligase is active on RNA substrates, as well as on DNA substrates (e.g., U.S. Pat. No. 5,807,674 of Tyagi), and is preferred for reporter probes having a first portion comprising RNA. If the parts of the first portion of the reporter probe comprise DNA mononucleosides, T4 DNA ligase, AMPLIGASE ligase (Epicentre Technologies, Madison, Wis., USA), Tth DNA ligase, Tfl DNA ligase, a type I topoisomerase (e.g., U.S. Pat. No. 5,766,891), or another composition having ligase activity can be used. An AND ligase, such as Ampligase ligase, Tth DNA ligase, or Tfl DNA ligase is preferred because those enzymes do not have activity in ligating DNA molecules having blunt ends, which decreases the likelihood of nonspecific ligation that causes background.

If the first portion of a reporter probe encodes only part of a substrate for replication by a replicase (e.g., one-half, one-third, or two-thirds of the substrate sequence is missing), the ligation method comprises ligation of the missing sequence to the sequence encoded by the first portion in order to generate a complete sequence for replication by a replicase. In some embodiments in which part of the substrate sequence is missing from a reporter probe having a first portion comprising DNA, a topoisomerase I-activated oligonucleotide or adapter can be used to generate the complete substrate sequence. In some embodiments, the topoisomerase-activated oligonucleotide or adapter can also comprise an RNA polymerase promoter (e.g., Yarovinsky, T. O., BioTechniques, 28: 1160–1165, 2000).

Generation of a Substrate for a Replicase from a Reporter Probe With a First Portion Comprising DNA by In Vitro Transcription Following release of the parts of the first portion of the reporter probe using a nuclease and ligation of the parts in the proper sequence, an RNA substrate for replication by a replicase can be generated from the first portion of the reporter probe by in vitro transcription from a double-stranded promoter sequence located at the 3'-end of the first portion. If the 3'-end of the most 3'-part of the first portion has a promoter sequence in a double-stranded (e.g., hairpin) structure, the first portion can be transcribed directly. If the promoter sequence is single-stranded, then a promoter-complementary oligonucleotide must be annealed to the promoter to make it double-stranded prior to in vitro transcription.

Conditions for performing in vitro transcription reactions are well known in the art, and many enzymes and kits for doing so are commercially available (e.g., SP6, T3 and T7 RNA polymerases, RIBOSCRIBE Kits, and AMPLISCRIBE SP6, T3 and T7 High-Yield Transcription Kits from Epicentre Technologies, Madison, Wis., USA) and can be used using protocols described in the literature or available from the manufacturer. Other commercial high-yield transcription kits, or "home brew" kits with T7 RNA polymerase and suitable reaction components (e.g., using conditions described in U.S. Pat. No. 5,256,555) can also be used. Those with skill in the art know that reaction conditions can be changed and empirically evaluated in order to improve yield or some other aspect of an assay. By way of example, but not of limitation, one can modify and evaluate the effects of changing buffer, pH, nucleotide concentration, divalent magnesium cation concentration, salt concentration and ionic strength, quantity of enzyme, temperature, and other variables of a reaction. Under suitable reaction conditions, including the presence of the necessary reagents, the synthesis of RNA transcripts will occur. If other enzymes are used, those with skill in the art will know how to develop and optimize reaction conditions for a particular assay. In certain cases, reagents can be added to increase the quantity of RNA transcripts. Preferably the synthesis of RNA transcripts will be carried out in the presence of a ribonuclease inhibitor, as for example, antibodies that bind to and inhibit adventitious ribonucleases, vanadyl-ribonucleoside complexes, or human placental ribonuclease inhibitor, in order to avoid possible degradation of the transcripts by any adventitious ribonuclease contaminant (e.g., see Sambrook, et al., Chapter 7.4, Molecular Cloning: A Laboratory Approach $2^{nd}$ ed., Cold Spring Harbor Laboratory Press, 1989).

Separation Methods

Following binding of a reporter probe to analyte, if analyte is present in the sample, it is usually preferable to separate reporter probe molecules that are bound to analyte from unbound reporter probes by "separation method," by which is meant "compositions and steps that results in separation of reporter probes that are bound to analyte from unbound reporter probes." Separation is preferred, but is not essential for all embodiments of the invention. By way of example, but not of limitation, particular compositions and configurations of reporter probes, which are preferred compositions and configurations, generate a signal in the assay only in the presence of an analyte that binds to the reporter probe under binding conditions. Still by way of example, but not of limitation, for particular configurations of reporter probes with both a first portion and a second portion comprising RNA mononucleosides, a release method comprising RNase H will release a polynucleotide encoded by the first portion of the reporter probe only if the second portion is bound to an analyte comprising DNA. Those compositions and configurations of reporter probes, and compositions and steps of a release method that result in release a substrate for replication by a replicase only in the presence of analyte are preferred. Such preferred reporter probes and release methods may be used in "homogeneous" assays of the invention, by which is meant "assays that do not require separation of bound reporter probes from unbound reporter probes prior to contacting bound reporter probes with release method." If assays of the invention are not homogeneous assays, then the use of a separation method is preferred.

The invention is not limited by the separation method used. Those with knowledge in the art know a number of compositions and/or methods which may be used as separation methods in assays for particular analytes. By way of example, but not of limitation, an antibody that has affinity for a site on an analyte that is different from the site to which the reporter probe binds can be used in a separation method. In that case, the antibody that is bound to analyte may be bound by a second antibody that is immobilized on a solid surface. Following washing to remove unbound reporter probes and other unbound components of the assay, the reporter probes or reporter probes bound to analyte can be separated from one or both of the antibodies and the surface by various means known in the art. Alternatively, various other molecules that have affinity for an analyte or a modified analyte, whether directly or indirectly, can be used in the separation method. Various other specific binding pairs, such as, but not limited to, biotin and streptavidin, digoxigenin and an antidigoxigenin antibody, or an oligonucleotide and its complement, can also be used. Those with knowledge in the art will know a specific binding pair that is appropriate for use in a separation method in assays of the invention for a particular analyte. For analytes comprising nucleic acids or polynucleotides, preferred separation methods of the invention use "capture probes."

Capture Probes

According to the invention, a "capture probe" is a probe that is not a reporter probe and that is used as part of a separation method to immobilize either analyte or reporter probeanalyte hybrids on the surface of a solid, wherein the analyte comprises a target nucleic acid or a target polynucleotide. A capture probe comprises at least DNA, RNA, or both DNA and RNA mononucleosides or modified mononucleosides, such as, but not limited to, 2'-O-methyl-or 2'-fluoro-nucleotides. The capture probe has: (1) a "head portion," at least a part of which is complementary to either (a) a polynucleotide sequence in the analyte, or (b) a second polynucleotide sequence, at least a part of which, is complementary to a polynucleotide sequence in the analyte; and (2) a "tail portion" which has a "capture method," which is a way to capture the capture probe on a surface, such that said capture does not interfere with hybridization of the head portion to an analyte or polynucleotide which is complementary to analyte; and (3) a method to separate a captured analyte from the surface in a controllable manner.

More then one capture probe can be used in order to increase the efficiency of immobilization or capture of the target nucleic acid or the reporter probe-target nucleic acid hybrid on the surface. If more than one capture probe is used, the head of each capture probe is complementary to a different sequence of the nucleic acid target, or the polynucleotide that is complementary to the target.

The capture probe (through the head portion) may be hybridized to the analyte, directly or indirectly, either prior to, at the same time as, or after the reporter probe is bound to analyte under binding conditions. It is desirable that the capture probe-target hybrids be stable, so that hybrids are not lost during the assay. Persons skilled in the art are able to select a sequence and hybrid length sufficiently long to withstand the processing conditions of a particular assay. Generally, capture probe-target hybrid lengths of 30–50 basepairs are used, which defines the length of the head (in nucleotides) of the capture probe.

The tail of the capture probe or probes is used to immobilize the capture probe and its hybrids to a solid surface, either permanently or reversibly. If separation of the capture probe or probes is used, a preferred embodiment uses a capture probe with a tail comprising a biotin group that will react with a streptavidin-coated solid surface. Between the head of a capture probe and its tail is a spacer, generally an oligonucleotide sequence. Preferred assays use hybridizations in solution, that is, when targets are not immobilized on a solid surface. Particularly for such preferred assays, the spacer may be quite short. Preferred spacers are 3–8 nucleotides in length, but longer spacers can also be used.

The capture probe (through the tail portion) can be immobilized on the surface, directly or indirectly, either prior to, at the same time as, or after the reporter probe is bound to analyte under binding conditions. By way of example, but not of limitation, the capture method can be a biotin moiety that is covalently attached to the tail portion, which can be captured by streptavidin moieties that are covalently attached to a surface. Alternatively, the capture method can be an oligonucleotide such as oligo(A) or oligo(dA) in the tail and oligo(dT) or oligo(T), respectively, attached to a surface. Preferred embodiments of the invention utilize solid surfaces having streptavidin covalently linked to the surface and capture probes that contain a biotin moiety. Those skilled in the art will recognize many possibilities for capture method, and all such methods known in the art are incorporated in the invention without limitation.

The type of solid surface on which the capture probe is immobilized is not critical. The solid can be a particle, including a magnetic or paramagnetic particle, a dipstick, a membrane, the well of a microtiter plate, or the surface of a tube, for example. Any appropriate immobilization technique can be used, depending on whether or not immobilization is to be permanent or reversible, as in reversible target capture (Morrissey, D. V., et al., Anal. Biochem., 181: 345–359, 1989; Hunsaker, W. R., etal., Anal. Biochem., 181: 360–370, 1989; Thompson, J., et al., Anal. Biochem., 181: 371–378, 1989). Dipsticks or reaction tubes (test tubes) may serve as the solid for an assay particularly adapted for performance under field conditions.

Analyte that is bound to a surface using a capture probe is separated by separation method only after binding of the reporter probe to the analyte under binding conditions and washing the surface to remove unbound reporter probes. Procedures for washing a solid phase are well known, including typically aspiration and decanting.

Separation is accomplished by cleaving into parts, and then isolating the parts. By "cleaving" is meant the breaking of at least one phosphodiester bond at an appropriate site or sites in the target or in the capture probe. The cleavage step and the cleaving agent or agents that are appropriate depend on the nature of the target nucleic acid, the nature of the capture probe, and the nature of the reporter probes, if present. In embodiments including separation from capture probes, preferred embodiments utilize cleavage with ribonuclease H ("RNase H"), which cleaves RNA that is hybridized to DNA. A DNA capture probe is utilized for an RNA target, in which case the target is cleaved. An RNA capture probe is utilized for a DNA target, in which case the capture probe is cleaved. Those skilled in the art will recognize many possibilities for separation of analytes captured on a surface using capture probes, and all such methods known in the art are included in the invention. By way of example, but not of limitation, separation of a capture probe can be achieved using: (1) a DNA capture probe designed with one or more deoxyuridine moieties, which can be cleaved with uracil-N-glycosylase and endonuclease IV; (2) a DNA capture probe designed with a rare-cutting restriction endonuclease site in a double-stranded hairpin in the tail portion; or (3) a DNA or RNA capture probe designed so that it will have a cleavage structure which can be cleaved using an invader oligonucleotide and a 5' nuclease. In general, a composition and steps comprising a nuclease which can be used as a release method can also be used as a separation method in embodiments of the invention.

Detection Methods

A "detection method" of the invention is a composition or method or a composition and method for detecting, whether directly or indirectly, the products of replication by a replicase from a method or assay of the invention. The method of detection is not critical. Any appropriate method of detection can be used, such as, but not limited to, radioactive counting or imaging, colorimetry, fluorescence or luminescence. Detection can be in real time, or over time for quantitative detection.

Replication by a replicase of the present invention produces RNA that can be detected using various methods. For example, the RNA can be directly detectable by addition of a labeled nucleotide in the replication reaction. In many situations, it may be preferred to use labeled UTP, since this nucleotide is specific to RNA molecules and hence its incorporation will be limited to RNA reaction products. Many different labels can be used in generating detectable RNA. For example, labeling RNA by incorporation of nucleotides containing radioactive $^{32}P$ or $^{35}S$ can be used. In addition, there are known non-radioactive techniques for signal amplification including methods for attaching chemical moieties to pyrimidine and purine rings (Dale, R. N. K., et al., Proc. Nat. Acad. Sci. USA, 70: 2238–2242, 1973; Heck, R. F., J. Am. Chem. Soc., 90: 5518–5523, 1968), methods that allow detection by chemiluminescence (Barton, S. K., et al., J. Am. Chem. Soc., 114: 8736–8740, 1992) and methods utilizing biotinylated nucleic acid probes (Johnson, T. K., et al., Anal. Biochem., 133: 125–131, 1983; Erickson, P. F., et al., J. of Immunology Methods, 51: 241–249, 1982; Matthaei, F. S., et al., Anal. Biochem., 157: 123–128, 1986) and methods that allow detection by fluorescence using commercially available products.

Unlabeled products of replication can also be detected in the present invention by many techniques known in the art. For example, a preferred method for detecting products of replication by a replicase of the present invention uses intercalating dyes, such as, but not limited to ethidium or propidium dyes, or other dyes, such as, but not limited to, SYBR Gold or SYBR Green (commercially available from Molecular Probes, Eugene, Oreg., USA) in the presence of ultraviolet light or in the presence of visible light using a DARKREADER transilluminator or similar technology (Clare Chemical Research, Denver, Colol., USA). The invention is not limited by the particular dye or type of dye, or the detection method used.

Probes that use hybridization for the detection of RNA can also be used to detect products of replication. For example, use of molecular beacons is another preferred method for detecting products of replication according to the present invention (Tyagi, S., et al., Nature Biotechnology, 16: 49–53, 1998). Also, a hybridization protection assay for RNA that is commercially available from Gen-Probe, Inc. (San Diego, Calif.) can be used. The hybridization protection assay employs a single-stranded nucleic acid probe linked to an acridinium ester, as described in U.S. Pat. No. 4,851,330. Hybndization of the probe to a target RNA molecule protects the acridinium ester bond from alkaline hydrolysis. Thus, the unhybridized probes are first destroyed by alkaline hydrolysis, and then the bound and protected acridium ester is detected by chemiluminescence. The chemiluminescent signal is proportional to the amount of hybridized RNA in the sample.

The RNA from replication can also be detected with the aid of an antibody specific for a labeled probe as described in U.S. Pat. No. 4,743,535 to Carrico. The probe is labeled with a detectable substance such as flavin adenine dinucleotide (FAD) or a fluorescent agent. An antibody specific for the labeled probe, after it has hybridized to sequence in the RNA product, is detected by a biochemical reaction.

Compositions and Kits of the Invention

The invention also includes compositions and kits for use in performing methods and assays according to the invention, including, but not limited to, at least one of the following items:

1. A reporter probe;
2. A replicase;
3. A composition having nuclease activity for use in a release method;
4. One or more oligonucleotides comprising sequence for a replicase substrate that is missing from the first portion of a reporter probe;
5. A composition having ligase activity for joining the released parts of the first portion and oligonucleotides encoding any substrate sequence that is missing from the first portion of the reporter probe;
6. For reporter probes having a first portion comprising DNA mononucleotides: An in vitro transcription system;
7. A capture probe for use in a separation method;
8. A reagent for use in a detection method;
9. A control substance for an analyte-specific assay; and/or
10. Instructions for performing an assay of the invention.

Those with skill in the art will know a variety of formats for providing compositions and kits for performing the methods and assays of the invention. The invention is not limited by the format or combination of the composition or kit provided. By way of example, but not of limitation, a composition or kit can be provided for assaying for only one analyte or for multiple analytes, whether for independent assays, or for multiplex assays. Thus, a kit can contain one or multiple reporter probes, nucleases for use in a release method, and/or capture probes for use in a separation method. Further, one method can comprise one or multiple compositions. By way of example, but not of limitation, a separation method can comprise one or more capture probes, RNase H, buffers and reagents, and optionally, a device such as, but not limited to, a dipstick, reaction tube, a microtiter plate, or paramagnetic particles, with a substance, such as, but not limited to, streptavidin covalently bound to its surface. Also, an in vitro transcription system can comprise multiple compositions, including a promoter-complementary oligonucleotide for making a double-stranded promoter.

EXAMPLES

The following prophetic examples are provided to illustrate and clarify, but not to limit, the compositions and methods of the invention. They are presented with the understanding that, based on empirical results and data obtained, changes can be and may need to be made to a specific composition or configuration of a reporter probe, capture probe, analyte-binding substance, release method, or to specific conditions of a method of an assay in order to obtain or optimize assay results for the analyte. Situations that could cause potential problems will be evaluated in a manner similar to that described in the section entitled "Evaluation and Modification of Reporter Probes," and appropriate modifications will be made. Such modifications to a prophetic example, if needed, are normal and understandable, and shall not be used to limit the invention.

Figure 3:
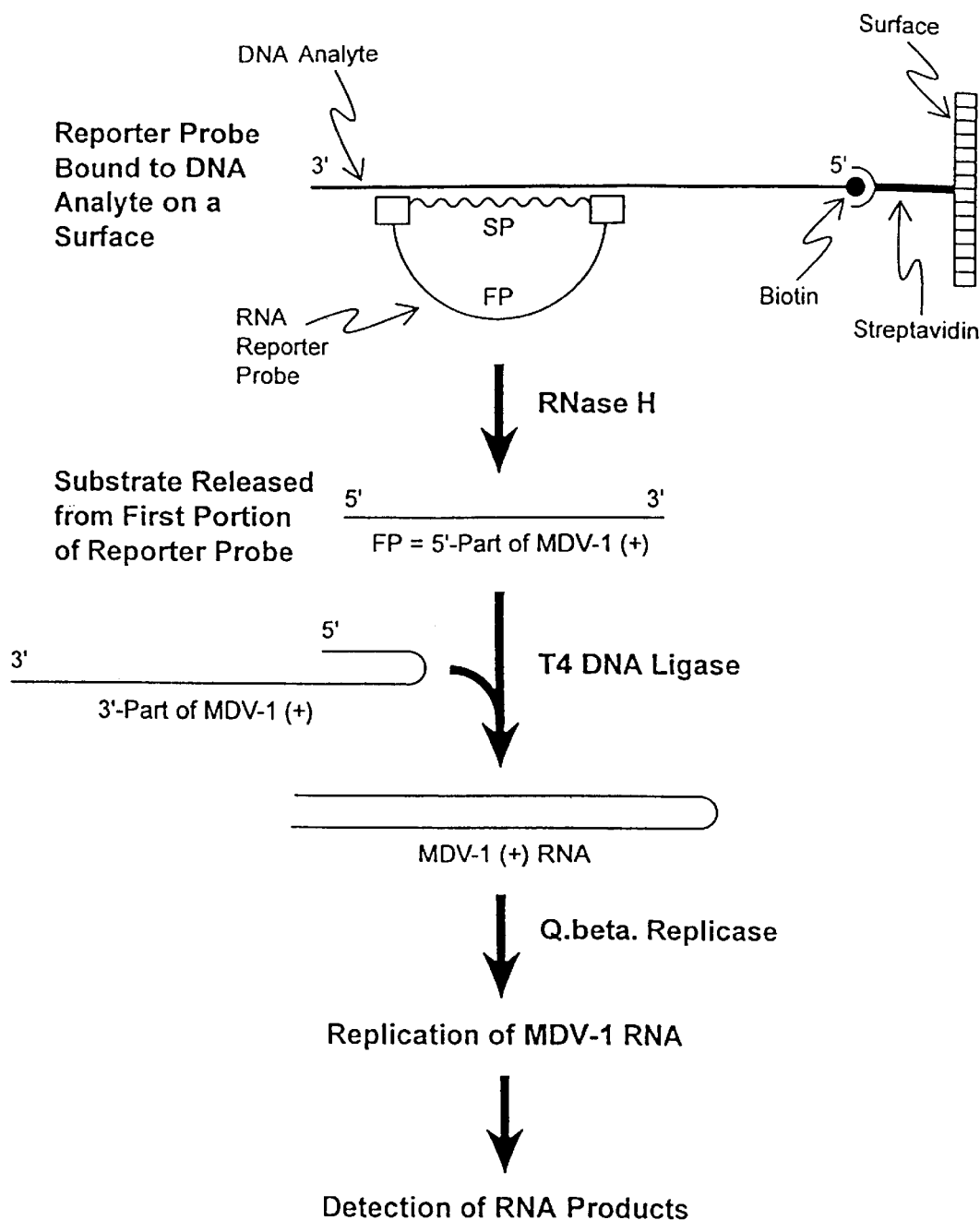
FIG. 3 depicts the assay of Example 1.
Figure 4:
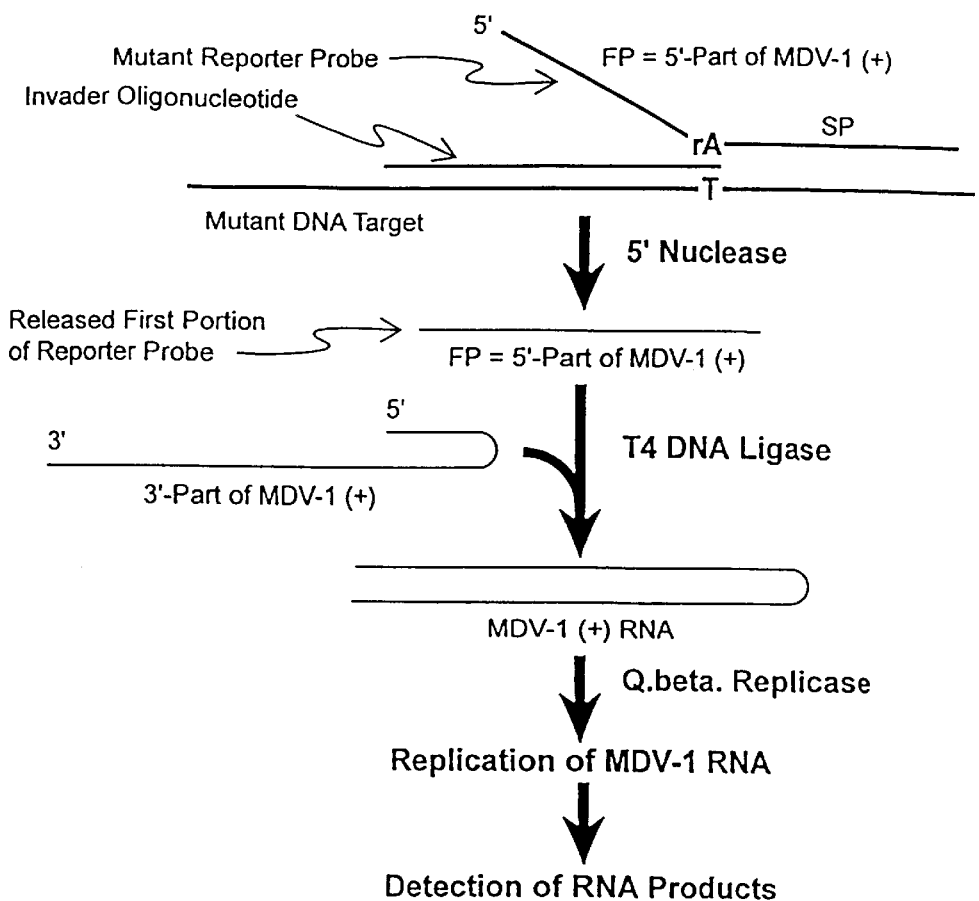
FIG. 4 depicts the assay of Example 2.
Figure 4:
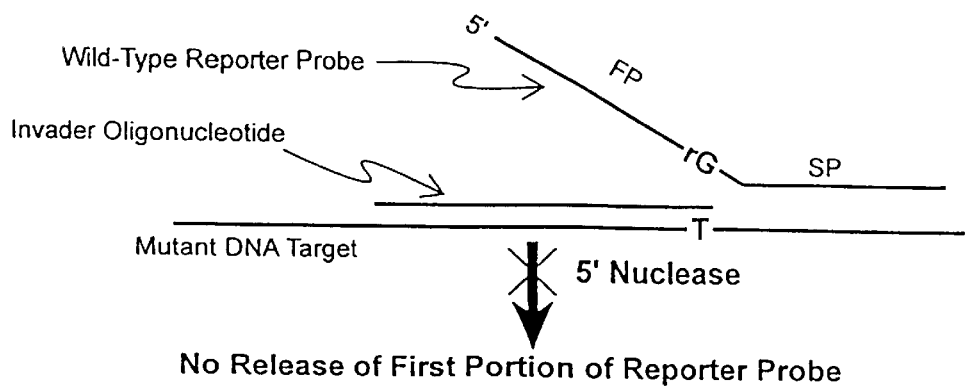

Example 1
DNA Target Analyte, RNA Reporter Probe of Configuration 2, Ribonuclease H as a Release Method Example 1 presents an embodiment of the invention for a polynucleotide target analyte comprising DNA (FIG. 3). The DNA can be present in an untreated sample (e.g., HBV or hepatitis B virus in human blood), or it can be a single-stranded or double-stranded cDNA that is prepared by reverse transcription of RNA in a sample. The cDNA can be prepared as a step in an assay of the invention. In some embodiments, a primer having a moiety for immobilization of the cDNA on a surface, such as, but not limited to a biotin moiety, can be used for making the cDNA; in those embodiments, the biotin moiety can be used to capture the cDNA-reporter probe hybrid on a surface, so a separate capture probe is not required. Example 1 muses a single-stranded cDNA that encodes the integrase gene of the human immunodeficiency virus (HIV); the example is for a cDNA prepared using a primer for first strand cDNA synthesis that is end-labelled with a biotin moiety. The assay of this example is performed on HIV-negative human blood samples to which known amounts of HIV integrase first strand cDNA is added as a model target.

Example 1 employs an RNA probe having configuration 2 as described in the section entitled "Configurations of Reporter Probes." This example shows an embodiment of an extremely simple assay of the invention, depicted generally in FIG. 3 for the detection of a DNA target analyte, illustrated here by HIV first strand cDNA. The target sequence is located in the integrase region of HIV RNA. The assay begins by dissolving the model sample, consisting of human blood containing different amounts of added HIV CDNA, in 5M guanidine thiocyanate (GuSCN), which dilutes the GuSCN to 2M. The reporter probe is then added to the sample. The reporter probe hybridizes to the HIV CDNA. After hybridization, the hybrids are captured on the surface of paramagnetic particles coated with streptavidin, which binds tightly to the biotin moiety at the 5'-end of the cDNA target analyte, as shown in FIG. 3. The paramagnetic particles are then washed extensively to remove unhybridized reporter probe molecules.

RNase H is then added as a release method. The RNase H digests the second portion of the reporter probe that is hybridized to the analyte. Theoretically, release is quantitative and specific. The reporter probes that nonspecifically adhere to the surface of the paramagnetic particles (i.e., sources of the background signal) are not released by this digestion. The paramagnetic particles are discarded. Assays utilizing this target-dependent release reduce nonspecific background and achieve an improved signal-to-noise ratio in a single step. Digestion of the second portion of the reporter probe releases the first portion of the reporter probe, comprising the first 99 nucleotides at the 5'-end of MDV- 1 (+) RNA, from reporter probe-target hybrids.

The released first portion of the reporter probe is ligated using T4 DNA ligase to an oligoribonucleotide comprising the missing nucleotides 100–221 at the 3'-end of MDV-1 (+) RNA. The homology between the first portion of the reporter probe and the oligoribonucleotide may be sufficient for ligation of the two molecules. If not, an oligodeoxynucleotide ligation template that is complementary to a segment at the 3'-end of the first portion of the reporter probe and the 5'-end of the oligoribonucleotide is used. Ligation generates an MDV-1 (+) substrate for replication by Q-beta replicase. Since the amount of substrate for replication released by RNase H is strictly dependent on the presence of the target, the level of the signal as a function of time can be used to quantify the number of molecules of HIV cDNA in the initial sample. The products of replication are detected and quantified by measuring fluorescence in the presence of SYBR Gold dye (Molecular Probes, Eugene, Oreg., USA).

A. Reporter Probe.

The reporter probe used in Example 1 is a linear molecule comprising RNA mononucleosides linked by phosphodiester internucleoside linkages. The first portion of the reporter probe comprises part of MDV-1 (+) RNA (e.g., see U.S. Pat. No. 4,786,600). The second portion of the reporter probe is a 22- to 44- nucleotide sequence that is complementary to cDNA for a region between nucleotides 4577 and 4618 of HIV genomic DNA. The assay is first performed with a shorter HIV-complementary sequence, in this case, a 22-nucleotide sequence comprising the region 4597–4618 of HIV genomic RNA. If this sequence does not yield sufficient specificity, a different and/or longer sequence, complementary to cDNA for the 4577–4618 region or another region, is used. The reporter probe and the oligoribonucleotide for the 3'-part of the MDV-1 (+) sequence that is missing from the first portion of the reporter probe are each prepared by in vitro transcription of DNA encoding the corresponding "reporter probe sequence" and oligoribonucleotide-complementary sequence, which are each cloned downstream of an SP6 RNA polymerase promoter in a pGEM plasmid vector (Promega, Madison, Wis., USA). The pGEM clones of the corresponding reporter probe sequence and oligoribonucleotide-complementary sequence are first linearized by incubation with a restriction enzyme that cuts at the 3'-end of the respective sequence. Then, RNA is made by run-off transcription of each linearized clone using an AMPLISCRIBE SP6 High Yield Transcription Kit according to the manufacturer's instructions (Epicentre Technologies, Madison, Wis., USA). SP6 RNA polymerase from other sources can also be used according to methods known in the art. For the purpose of this example, the linear reporter probe sequence obtained by in vitro transcription comprises, starting from its 5'-end, the first 99 nucleotides of the 5'-end of the MDV-1 (+) sequence, followed by 22 nucleotides of the HIV sequence (i.e., 4597–4618 of HIV genomic RNA). The oligoribonucleotide sequence comprises the remaining sequence, in this case, nucleotides 100–221 at the 3'-end of the MDV-1 (+) sequence. The inability of both the reporter probe and the oligoribonucleotide encoding the 3'-part of MDV-1 (+) to replicate in the presence of Q-beta replicase are evaluated; if replication occurs, the number of nucleotides of 5'-MDV-1 (+) sequence in the first portion of the reporter probe and in the oligoribonucleotide are modified so that replication does not occur. The linear RNA products are treated with TAP (i.e., tobacco acid pyrophosphatase, from Epicentre) to convert the 5'-triphosphate to a 5'-phosphate. The RNAs are purified by preparative denaturing polyacrylamide gel electrophoresis (PAGE.

B. Sample

The assay of this example is performed on a model system consisting of blood samples containing known amounts of HIV first strand CDNA molecules. A cDNA corresponding to the mRNA of the integrase gene of HIV is used as a model target. This cDNA is prepared by reverse transcription of the HIV RNA integrase gene using a primer having a biotin moiety at its 5'-end. The resulting first strand cDNA is used to prepare model samples. Eight tubes containing differing amounts, for example, 10000000, 1000000, 100000, 10000, 1000, 100, 10, and 0 molecules, of integrase cDNA in 50 microliters of HIV-negative human blood containing 2M GuSCN are prepared by serial dilution.

C. Hybridization, Capture, Washing, and Release

A 2M GuSCN solution (50 microliters) containing $10^{10}$ molecules of the reporter probe is added to each sample tube. The optimal hybridization temperature for the assay is determined empirically. Initially, hybridization is carried out by incubation at 37° C. for one hour. If the stringency is not adequate, stringency is increased or decreased by using a higher or lower temperature, respectively. A 30-microliter suspension of paramagnetic particles coated with streptavidin (Promega Corporation, Madison, Wis., USA) is then added to this hybridization mixture. The reporter probe-target hybrids are captured on the surface of the paramagnetic particles by a 10-minute incubation at 37° C. The particles are washed with 2M GuSCN four times, with 300 mM KCl three times, and finally with 1.times. TA Buffer (33 mM Tris-acetate, pH 7.8, 66 mM potassium acetate, 10 mM magnesium acetate, and 0.5 mM dithiothreitol) two times. After washing, *E. coli* RNase H (Epicentre) dissolved in 50 microliters of 1.times. TA Buffer is added. The parts of the first portion of the reporter probe are released from the reporter probe-target hybrids attached to the surface of the paramagnetic particles by a 10-minute incubation at 37° C. The tubes containing the mixture are placed in the magnetic field provided by a magnetic separation device to draw the paramagnetic particles to the walls of the test tubes. The supernatant is then separated from the paramagnetic particles by aspiration and placed into a fresh tube. The tubes are incubated at 70° C. for 15 minutes in order to inactivate RNase H. Then, one volume of the supernatant is added to one volume of a 2.times. TA Buffer containing $2\times10^{10}$ molecules of the oligoribonucleotide corresponding to the 3'-end of MDV-1 (+) RNA, and 10–80 Weiss units of T4 DNA ligase, 2 mM ATP, (and, if necessary, $2\times10^{10}$ molecules of a 24-mer oligonucleotide ligation template that has 12 nucleotides which are complementary to the 3'-end of the first portion of the reporter probe and 12 nucleotides which are complementary to the 5'-end of the oligoribonucleotide). Ligation conditions, such as time and temperature of the ligation reaction, are established for use in an assay by monitoring ligation of known amounts of the particular substrates by PAGE analysis. Following ligation of the released first portion and the oligoribonucleotide comprising the 3'-end of MDV-1 (+) RNA, the ligation product can be used in a replication reaction using Q-beta replicase.

D. Replication by Q-beta Replicase

The MDV-1 (+) molecules are then amplified by incubation with Q-beta replicase. A mixture containing all of the components of the replication reaction is added to each reaction tube. The final reaction mixture (120 microliters) is 45 mM Tris-HCl, pH 8, 10 mM $MgCl_2$, 400 micromolar each of ATP, GTP, UTP, and CTP, and 50 micrograms per milliliter Q-beta replicase. (If desired, an alpha-$^{32}P$ -labeled NTP can be used to monitor replication.) Each reaction is incubated at 37° C., and 4-microliter samples are withdrawn from each reaction every minute in the interval between 10 to 60 minutes of incubation. Each sample is mixed with a 45-microliter stop solution (120 mM NaCl, 20 mM EDTA, and 3 microgram per ml proteinase K). This solution stops replication by sequestering the required magnesium ions. The stop solutions are arranged in titerplates before addition of the samples. The RNA in each stopped reaction is separated from the unincorporated nucleoside triphosphates by precipitating the RNA in an acidic solution (360 mM phosphoric acid, 20 mM sodium pyrophosphate, and 2 mM EDTA). If radioactive NTP is used, the precipitate is trapped on a blotting membrane (Zeta Probe, Biorad), the membrane is washed with the acidic solution, and the RNA on the blots is visualized by autoradiography. If radioactive label is not used, the precipitate is dissolved in water and quantified using SYBR Gold dye (Molecular Probes, Inc., Eugene, Oreg.) or an ethidium or propidium dye. This can be done by agarose gel electrophoresis of equal size aliquots from each sample versus known standards, staining of the gel with SYBR Gold, and comparing fluorescence versus standards on a DARKREADER visible light transilluminator (Clare Chemical Research, Denver, Colo., USA). If an ethidium or propidium dye is used, the DarkReader transilluminator or an ultraviolet transilluminator can be used. Preferably, a detectable signal is obtained from samples containing analyte after an incubation time of one hour or less.

Example 2

DNA Target Analyte, RNA Reporter Probes of Configuration 1, and an INVADER Oligonucleotide and a 5' Nuclease as a Release Method Example 2 shows an embodiment of a simple assay of the invention for detection of the single-base factor V Leiden mutation in genomic DNA, as depicted in FIG. 4. The target analyte illustrated here is the factor V Leiden mutation in human genomic DNA. This mutation is present in 3–6% of the general population and is the most common genetic risk factor for venous thrombosis (Dahlback, B., Haemostasis, 24: 139–151, 1994). The mutation involves a single G-to-A mutation that changes an arginine to a glutamine in the protein and alters the activated protein C cleavage sites on Factor Va (Bertina, R. M., et al., Nature, 369: 64–67, 1994).

An Invader assay for factor V is available from Third Wave Technologies (Madison, Wis., USA) that gives good specificity and acceptable signal with 70 ng or more of genomic DNA per reaction. However, the signal is unacceptable with less than 70 ng of genomic DNA per reaction (Ryan, D., et al., Molecular Diagnosis, 4: 135–144, 1999). Assays of the present invention can be used with an INVADER oligonucleotide and a 5' nuclease as a release method. Without being bound by theory, the inventor believes that homogeneous assays that use the present invention and an invader oligonucleotide and 5' nuclease as a release method have good specificity and are more sensitive, yielding acceptable signal with less than 70 ng of sample genomic DNA per reaction. Whether or not this theory is correct, Example 2 illustrates embodiments of the present invention which use an RNA reporter probe, as well as other aspects of the invention.

Example 2 employs a linear single-stranded RNA probe having configuration 1 as described in the section entitled "Configurations of Reporter Probes." Two linear single-stranded reporter RNA probes having configuration 1 are used, one for the mutant allele (the "mutant reporter probe") and one for the wild type allele (the "wild type reporter probe"). The mutant and the wild type reporter probes have a first portion comprising, respectively, 92 or 93 nucleotides of the 5'-end of MDV-1 (+) RNA (ending in an A or a G, respectively), and a second portion comprising a 23–24 nucleotides which are complementary to the region 3' of the factor V gene mutation. The only difference between the two reporter probes is that the 3'-end of the first portion of the mutant reporter probe is adenosine ribonucleotide (complementary to the mutant allele), whereas the 3' end the first portion of the wild type reporter probe is guanosine ribonucleotide (complementary to the wild type allele). The assay is performed by first hybridizing separate aliquots of sample genomic DNA with each of the reporter probes and an INVADER oligonucleotide which has one base of invasion into the A or G nucleotide of the mutant or wild type reporter probes, respectively. The hybrids are incubated with a 5' nuclease as a release method. Under appropriately stringent hybridization conditions, the first portion of the reporter probe, comprising the 5'-part of a substrate for Q-beta replicase, is released from the reporter probe only if the allele that is complementary to the respective reporter probe is present in the sample. The released first portion is then ligated to the respective 3'-part of the MDV-1 (+) RNA sequence in order to generate a complete substrate. After incubation with Q-beta replicase, a signal is detected indicating the presence of the respective mutant and/or wild type allele in the sample.

A. Reporter Probes.

The reporter probes are prepared by in vitro transcription of mutant and wild type "reporter probe sequence" that is cloned in a plasmid downstream of a T3 RNA polymerase promoter. The mutant reporter probe clone comprises a sequence that encodes, at the 5'-end of the resulting T3 RNA polymerase transcript, the first 92 nucleotides (ending in an adenine) at the 5'-end of MDV-1 (+) RNA (U.S. Pat. No. 4,786,600), followed by 23–24 nucleotides complementary to the factor V sequence. Including the 3'-nucleotide of the first portion of the reporter probe, this sequence begins with 5' AAGGA3' for the mutant reporter probe and with 5' GAGGA3' for the wild type reporter probe. In this example, the total number of ribonucleotides and deoxyribonucleotides comprising the second portion of the reporter probe is about 24 nucleotides. In one embodiment, a biotin moiety is attached to the 3'-end of the second portion of the reporter probes in order to be able to separate reporter probes from the released first portion by binding to a surface with streptavidin.

B. Sample

The sample used for analysis in Example 2 is leukocyte genomic DNA that is extracted from either EDTA- or citrate-anticoagulated peripheral blood from patient or control subjects. This genomic DNA is extracted from the buffy coat as described by Ryan, et al. (Molecular Diagnosis, 4: 135–144, 1999), or using a buffy coat protocol for the MASTERPURE DNA Purification Kit (Epicentre Technologies, Madison, Wis., USA) and the resulting DNA is quantified using a PICOGREEN dsDNA kit (Molecular Probes, Inc., Eugene, Oreg., USA) according to the manufacturers' instructions. All samples are assayed in separate reactions with both wild type and mutant reporter probes, with each reaction performed in replicate.

C. Hybridization and Release Using an Invader Oligonucleotide and a 5' Nuclease

An assay of Example 2 is performed as follows: Eight microliters of an Invader Reaction Mix (5 microliters of 16% PEG [8000 MW], 2 microliters of 100 mM MOPS, and 1 microliter of 0.5 micromolar invader oligodeoxynucleotide) is pipetted into each well of a 96-well reaction microplate; the Invader Reaction Mix provided in a commercially available kit from Third Wave Technologies (Madison, Wis., USA) for detecting the factor V Leiden mutation, including the invader oligonucleotide, is used exactly as provided. Then, 7 microliters of a genomic DNA sample is added to each of replicate wells for each of 3 DNA levels (50 ng, 100 ng, 150 ng) for a sample. Four types of control samples are used: (1) no DNA; (2) homozygous wild type DNA; (3) homozygous mutant DNA; and (4) heterozygous wild type/mutant DNA. Samples are incubated at 95° C. for 5 minutes in a model PTV-100 thermocycler (MJ Research, Watertown, Mass., USA). The optimal hybridization temperature for the assay is determined empirically. If the stringency is not adequate in the first assay, stringency is increased or decreased by using a higher or lower temperature, respectively. In this example, the temperature is lowered to the initial hybridization temperature of 63° C. and 5 microliters of a 5' nuclease/$Mg^{2+}$/reporter probe mix (1 microliter water; 1 microliter of 10 micromolar wild type or mutant reporter probe; 2 microliters of 75 mM $MgCl_2$; 1 microliter of 100 ng/microliter Cleavase VIII enzyme) is added to each well; all components are as provided in the Third Wave Technologies' kit except that the mutant and wild type reporter probes of the present invention, as described above, are used in place of the Mutant and Wild Type probes provided by Third Wave Technologies. The reaction mixture is incubated at 63° C. for two hours. The results of this assay are also compared with results obtained for assays which are incubated for shorter times (e.g., for 30, 60, and 90 minutes) and at different lower temperatures between 40° C. and 63° C. Then, for this example, an antibody is added to inhibit the 5' nuclease following the incubation step for hybridization and release. Without being bound by theory, the inventor believes, as discussed previously, that the 5' nuclease will usually need to be inhibited, inactivated, or removed prior to replication so that the 5' nuclease does not cleave the RNA products during exponential sythesis. If empirical results show that this step is not necessary, it will be omitted. In this example, the 5' nuclease is inhibited by addition of an antibody that binds to and inhibits its activity, and then the 5' nuclease is removed from the reaction by binding of the inhibitory antibody to a second antibody which is attached to a surface of a tube or microtiter well.

D. Ligation to Generate a Substrate for Replication by Q-beta Replicase

The released first portion of the reporter probe is ligated to the missing 3'-part of the MDV-1 (+) RNA, comprising nucleotides 93–221 for the mutant reporter probe and nucleotides 94–221 for the wild type reporter probe, using T4 DNA ligase as describe previously. Ligation templates are used if needed.

E. Replication by Q-beta Replicase

Replication using Q-beta replicase is performed as described previously. Products of replication are detected using SYBR Gold (Molecular Probes, Eugene, Oreg., USA) or another suitable method for detecting RNA.

Example 3

An Analyte (e.g., a Protein) That Is Not a Nucleic Acid, an RNA Reporter Probe of Configuration 1 with a Second Portion Comprising an Analyte-Binding Substance Obtained by SELEX, an Antibody as a Capture Probe and an Oligodeoxynucleotide and RNase H as a Release Method.

Figure 5:
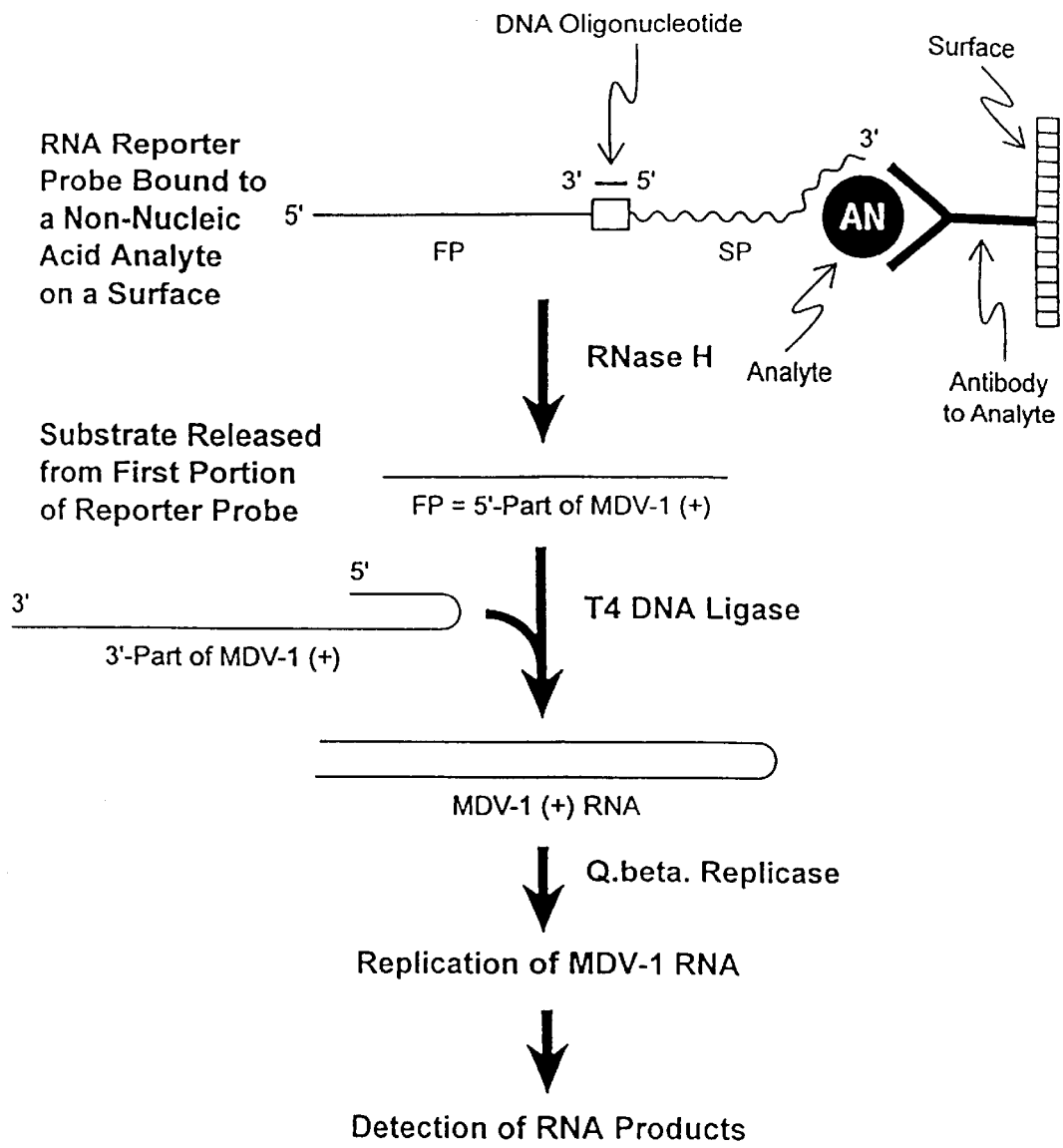
FIG. 5 depicts the assay of Example 3.

Example 3 illustrates an embodiment of the invention for detection of non-nucleic acid analytes, as shown in FIG. 5. In this example, the RNA reporter probe comprises a first portion that encodes the first 99 nucleotides at the 5'-end of MDV-1 (+) RNA, linked by an oligoribonucleotide linker as a joining method to a second portion comprising an RNA that is an analyte-binding substance obtained using SELEX that binds to the analyte. The reporter probe is incubated with a sample containing analyte under binding conditions in a tube or a well of a microtiter plate. The inside surface of the tube or well in which the binding reaction is performed also has an attached antibody that binds to a site on the analyte that is different than the site to which the analyte-binding substance binds. At the end of the binding the reaction, the reaction mixture is removed and the tube or well is washed thoroughly. An oligodeoxynucleotide that is complementary to the joining method and RNase H are added as a release method. The solution containing the RNA released from the first portion of the bound reporter probes is then transferred to a new unmodified tube or microtiter plate well for ligation (as described previously) to an oligoribonucleotide comprising the missing nucleotides 100–221 at the 3'-end of MDV-1 (+) RNA. Following ligation, the solution is incubated with Q-beta replicase for replication of the MDV-1 (+) substrate. The RNA product indicates the presence and, if controls are used, the quantity of analyte in the sample.

A. Reporter Probes.

The reporter probe is prepared by in vitro transcription from a clone or PCR product using similar techniques to those described previously. The reporter probe comprises the first 99 nucleotides at the 5'-end of MDV-1 (+) joined to a linker oligoribonucleotide by a phosphodiester bond, which is further linked at its 3'-end by a phosphodiester bond to an oligoribonucleotide that is identified using SELEX (e.g., U.S. Pat. No. 5,270,163). The ability of the analyte-binding substance to bind to analyte when it is part of the reporter probe is verified empirically before the reporter probe is used for assays.

B. Sample

Those with skill in the art know many samples that are appropriate for use in an assay of this example, such as, but not limited to, cell extracts.

C. Binding, Release, and Ligation

Those with skill in the art know conditions appropriate for binding of an analyte of this example, use of an oligodeoxynucleotide and RNase H as a release method, and ligation of the oligoribonucleotide to the released first portion of the reporter probe, as are also described in greater detail elsewhere herein.

D. Replication by Q-beta Replicase

Replication by Q-beta replicase and detection of products are performed using techniques similar to those described previously herein.

I claim:

1. A method for assaying for an analyte in a sample comprising the steps of:

(a) incubating a sample with a reporter probe under conditions and for a time so as to permit binding of said reporter probe with analyte, if present in sample, said reporter probe comprising a first portion, wherein said first portion is a polynucleotide that encodes at least part of a sequence for a replicase substrate, and a second portion, wherein said second portion has affinity for the analyte under binding conditions, and wherein said reporter probe is not a substrate for replication by said replicase; and (b) incubating said reporter probe which binds to analyte with a composition having nuclease activity, wherein said composition releases all parts of said first portion of said reporter probe from said second portion of said reporter probe; and (c) incubating said released parts of said first portion of said reporter probe with a composition having ligase activity so as to form a polynucleotide which encodes a complete substrate for replication by a replicase, and providing conditions so as to generate said substrate; and (d) incubating said substrate with a replicase under replication conditions; and (e) detecting the products of said replication.

2. The method of claim 1 wherein said reporter probe which binds to analyte, if analyte is present in sample, is separated from unbound reporter probe prior to forming a substrate for replication by a replicase.

3. The method of claim 1 wherein said substrate for replication, for which said first portion of said reporter probe encodes at least a part, comprises a substrate for Q-beta replicase and said replicase is Q-beta replicase.

4. The method of claim 1 wherein said substrate for replication, for which said first portion of said reporter probe encodes at least a part, comprises a substrate for a replicase selected from the group consisting of Q-beta replicase, MS2 replicase, SP replicase, T7 RNA polymerase, T7-like RNA polymerase, and a replicase from an RNA virus that infects eucaryotic cells, and said replicase is the enzyme for which said first portion of said reporter probe encodes a substrate.

5. The method of claim 1 wherein said reporter probe comprises an analyte-binding substance for an analyte that comprises a nucleic acid.

6. The method of claim 1 wherein said reporter probe comprises an analyte-binding substance for an analyte that does not comprise a nucleic acid.

7. The method of claim 1 wherein said reporter probe comprises an analyte-binding substance that is selected using SELEX.

8. The method of claim 1 wherein said reporter probe comprises an analyte-binding substance that comprises a peptide nucleic acid (PNA).

9. The method of claim 1 wherein said reporter probe comprises an analyte-binding substance selected from the group consisting of amino acids, peptides, proteins, carbohydrates, polysaccharides, lipids, and small organic and inorganic chemical molecules.

10. The method of claim 1 wherein said composition having nuclease activity is an enzyme that has ribonuclease H (RNase H) activity.

11. The method of claim 1 wherein said composition having nuclease activity is an enzyme that has 5' nuclease activity.

12. The method of claim 1 wherein said composition having nuclease activity is a nucleic acid repair enzyme.

13. The method of claim 1 wherein said composition having nuclease activity is in the endonuclease III family of enzymes.

14. The method of claim 1 wherein said composition having nuclease activity is one or more enzymes having DNA glycosylase or AP cleaving activities.

15. The method of claim 1 wherein said composition having nuclease activity is one or more enzymes having uracil-N-glycosylase or AP cleaving activities.

16. The method of claim 1 wherein said composition having nuclease activity is a ribozyme.

17. The method of claim 1 wherein said composition having ligase activity comprises a nucleic acid ligase.

18. The method of claim 1 wherein said composition having ligase activity is selected from the group consisting of T4 DNA ligase, T4 RNA ligase, AMPLIGASE DNA ligase, Tth DNA ligase, Tfl DNA ligase, Pfu DNA ligase, *E. coli* DNA ligase, and a ribozyme ligase.

19. The method of claim 1 wherein a substrate for replication is formed by a method comprising in vitro transcription.

20. The method of claim 1 wherein said reporter probe comprises nucleic acid.

21. The method of claim 1 wherein said reporter probe comprises ribonucleic acid.

22. The method of claim 1 wherein said reporter probe comprises deoxyribonucleic acid.

* * * * *